United States Patent
Yamano

(10) Patent No.: US 10,294,302 B2
(45) Date of Patent: *May 21, 2019

(54) THERAPEUTIC METHOD AND MEDICAMENT FOR HTLV-1 ASSOCIATED MYELOPATHY

(71) Applicants: St. Marianna University School of Medicine, Kawasaki-shi, Kanagawa (JP); KYOWA HAKKO KIRIN CO., LTD, Tokyo (JP)

(72) Inventor: Yoshihisa Yamano, Kawasaki (JP)

(73) Assignees: ST. MARIANNA UNIVERSITY SCHOOL OF MEDICINE, Kawasaki-shi, Kanagawa (JP); KYOWA HAKKO KIRIN CO., LTD, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/475,367

(22) Filed: Mar. 31, 2017

(65) Prior Publication Data

US 2017/0204189 A1 Jul. 20, 2017

Related U.S. Application Data

(63) Continuation of application No. 13/936,290, filed on Jul. 8, 2013, now Pat. No. 9,642,910.

(Continued)

(51) Int. Cl.
*A61K 39/00* (2006.01)
*C07K 16/28* (2006.01)
(Continued)

(52) U.S. Cl.
CPC ........ *C07K 16/2866* (2013.01); *A61K 31/436* (2013.01); *A61K 31/52* (2013.01);
(Continued)

(58) Field of Classification Search
None
See application file for complete search history.

(56) References Cited

U.S. PATENT DOCUMENTS 6,989,145 B2   1/2006   Shitara et al.
7,504,104 B2   3/2009   Shitara et al.
(Continued)

FOREIGN PATENT DOCUMENTS

JP   2010-017130 A   1/2010
JP   2010-100578 A   5/2010

OTHER PUBLICATIONS

Araya, et al.; "Human T-Lymphotropic Virus Type 1 (HTLV-1) and Regulatory T Cells in HTLV-1-Associated Neuroinflammatory Disease", Viruses, Published Aug. 25, 2011, vol. 3, p. 1532-1548.

(Continued)

*Primary Examiner* — Janet L Andres
*Assistant Examiner* — Stuart W Snyder
(74) *Attorney, Agent, or Firm* — Sughrue Mion, PLLC

(57) ABSTRACT

The object of the present invention is to provide a new therapeutic method and a new therapeutic agent that are different from known therapeutic medicines for human T cell leukemia virus type-1 (also known as human T lymphotropic virus type-1) associated myelopathy (HAM) patients and asymptomatic HTLV-1 carriers. The present invention relates to a therapeutic method and a therapeutic agent for human T cell leukemia virus type-1 (HTLV-1) associated myelopathy (HAM) patients and asymptomatic HTLV-1 carriers (ACs), which is characterized by reducing HTLV-1 virus-infected cells using an anti-human CC-chemokine receptor 4 (CCR4) antibody.

18 Claims, 18 Drawing Sheets

Related U.S. Application Data

(60) Provisional application No. 61/668,686, filed on Jul. 6, 2012.

(51) Int. Cl.

| | | |
|---|---|---|
| A61K 31/573 | (2006.01) | |
| A61K 31/56 | (2006.01) | |
| A61K 39/395 | (2006.01) | |
| A61K 45/06 | (2006.01) | |
| A61K 38/13 | (2006.01) | |
| A61K 31/436 | (2006.01) | |
| A61K 31/52 | (2006.01) | |

(52) U.S. Cl.
CPC ............ *A61K 31/56* (2013.01); *A61K 31/573* (2013.01); *A61K 38/13* (2013.01); *A61K 39/3955* (2013.01); *A61K 39/3955* (2013.01); *A61K 45/06* (2013.01); *A61K 2039/505* (2013.01); *C07K 2317/21* (2013.01); *C07K 2317/24* (2013.01); *C07K 2317/73* (2013.01)

(56) References Cited

U.S. PATENT DOCUMENTS

| | | | |
|---|---|---|---|
| 9,642,910 B2* | 5/2017 | Yamano | A61K 39/3955 |
| 2003/0175273 A1 | 9/2003 | Shitara et al. | |
| 2010/0310464 A1 | 12/2010 | Cicortas Gunnarsson et al. | |
| 2011/0262431 A1 | 10/2011 | Ishii et al. | |

OTHER PUBLICATIONS

Gessain, et al.; "Antibodies to Human T-Lymphotropic Virus Type-I in Patients with Tropical Spastic Paraparesis", The Lancet, Published Aug. 24, 1985, pp. 407-409.

Ishii, et al.; "Defucosylated Humanized Anti-CCR4 Monoclonal Antibody KW-0761 as a Novel Immunotherapeutic Agent for Adult T-cell Leukemia/Lymphoma", Clinical Cancer Research, Published Feb. 16, 2010, vol. 16, No. 5, pp. 1520-1531.

Kaplan, et al.; "The Risk of Development of HTLV-I-Associated Myelopathy/Tropical Spastic Paraparesis Among Persons Infected with HTLV-I", Journal of Acquired Immune Deficiency Syndromes, Published 1990, vol. 3, No. 11, pp. 1096-1101.

Nagai, et al.; "Increased Activated Human T Cell Lymphotropic Virus Type I (HTLV-I) Tax11-19-Specific Memory and Effector $CD8^+$ Cells in Patients with HTLV-I-Associated Myelopathy/Tropical Spastic Paraparesis: Correlation with HTLV-I Provirus Load", The Journal of Infectious Diseases, Published Jan. 15, 2001, vol. 183, p. 197-205.

Nakagawa, et al.; "HTLV-I-Associated Myelopathy: Analysis of 213 Patients Based on Clinical Features and Laboratory Findings", Journal of NeuroVirology, 1995, vol. 1, p. 50-61.

Niwa, et al.; "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma", Cancer Research, Published Mar. 15, 2004, vol. 64, p. 2127-2133.

Nose, et al.; "Clinical Symptoms and the Odds of Human T-cell Lymphotropic Virus Type 1-Associated Myelopathy/Tropical Spastic Paraparesis (HAM/TSP) in Healthy Virus Carriers: Application of Best-Fit Logistic Regression Equation Based on Host Genotype, Age, and Provirus Load", Journal of NeuroVirology, 2006, vol. 12, p. 171-177.

Ohsugi, et al.; "Low CD4/CD8 T-Cell Ratio Associated with Inflammatory Arthropathy in Human T-Cell Leukemia Virus Type I Tax Transgenic Mice", Public Library of Science One, Published Apr. 1, 2011, vol. 6, Issue 4, p. 1-15.

Uchiyama, et al.; "Adult T-Cell Leukemia: Clinical and Hematologic Features of 16 Cases", Blood, 1977, vol. 50, No. 3, p. 481-492.

Yamano, et al. "Abnormally High Levels of Virus-Infected $IFN-Y^+$ $CCR4^+CD4^+CD25^+$ T Cells in a Retrovirus-Associated Neuroinflammatory Disorder", Public Library of Science One, Published Aug. 5, 2009, vol. 4, Issue 8, p. 1-14.

Yamano, et al.; "Correlation of Human T-Cell Lymphotropic Virus Type 1 (HTLV-1) mRNA with Proviral DNA Load, Virus-Specific $CD8^+$ T Cells, and Disease Severity in HTLV-1-Associated Myelopathy (HAM/TSP)", Blood, Published Jan. 1, 2002, vol. 99, No. 1, p. 88-94.

Yamano, et al.; "Virus-Induced Dysfunction of $CD4^+CD25^+$ T Cells in Patients with HTLV-I-Associated Neuroimmunological Disease", The Journal of Clinical Investigation, 2005, vol. 115, No. 5, p. 1361-1368.

Matsuura, et al.; "Neuroimmunity of HTLV-I Infection", Journal of Neuroimmune Pharmacology, Published May 2, 2010, vol. 5, p. 310-325.

Yamano, et al.; "Increased Expression of Human T Lymphocyte Virus Type I (HTLV-I) Tax11-19 Peptide-Human Histocompatibility Leukocyte Antigen A*201 Complexes on $CD4^+CD25^+$ T Cells Detected by Peptide-specific, Major Histocompatibility Complex-restricted Antibodies in Patients with HTLV-I-associated Neurologic Disease", The Journal of Experimental Medicine, Published May 17, 2004, vol. 199, No. 10, p. 1367-1377.

International Searching Authority, Communication dated Sep. 24, 2013, issued in corresponding International Patent Application No. PCT/JP2013/068296.

Araya et al. "Research on Development of New Medicines for HTLV-1 Associated Myelopathy (HAM) and Verification of Anti-Human CCR4 Antibody Immunotherapy in HTL V-1 Associated Myelopathy (HAM)", Year 2011 Summary-Sharing Research Report of the research on development of new medicines for HTLV-I associated myelopathy (HAM), Feb. 8, 2012, 13 pages total.

International Searching Authority, Communication dated Nov. 5, 2014, issued in corresponding International Patent Application PCT/JP2013/068296.

International Searching Authority, Communication dated Feb. 5, 2014, issued in corresponding International Patent Application No. PCT/JP2013/068296.

J. Yamauchi, et al., "Mogamulizumab, an Anti-CCR4 Antibody, Targets Human T-Lymphotropic Virus Type 1-infected $CD8_+$ and $CD4_+$ T Cells to Treat Associated Myelopathy", Journal of Infectious Diseases Advance Access published Sep. 9, 2014, JID, vol. 211, No. 2, 7, pp. 238-248, XP55236791.

European Patent Office, Communication dated Jan. 8, 2016 in a counterpart European Application No. 13813070.3.

Haynes, et al. Cyclosporine-induced immune suppression alters establishment of HTLV-1 infection in a rabbit model. Blood, 2010; 115(4): 815-823.

Ishida and Ueda, "Antibody therapy for Adult T-cell leukemia-lymphoma", Int J Hematol (2011) 94:443-452.

Kchour et al. "Phase 2 study of the efficacy and safety of the combination of arsenic trioxide, interferon alpha, and zidovudine in newly diagnosed chronic adult T-cell leukemia/lymphoma (ATL)", Blood, 2009; 113(26): 6528-6532.

Demontis et al. The clinical utility of HTLV-1 viral load Measurement. Retrovirol. 2011; 8(Suppl1):A:46.

K. Tobinai Seminars in Hematology, 2010; 47(2, Supl. 1): S5-S7.

Office Action dated Jan. 8, 2019 by the Japanese Patent Office in counterpart Japanese Patent Application No. 2018-049779.

* cited by examiner

* P < 0.05,  P < 0.01, * P < 0.001 versus PBMC only
ns, not significant

* P < 0.05,  P < 0.01, * P < 0.001 versus PBMC only
ns, not significant

THERAPEUTIC METHOD AND MEDICAMENT FOR HTLV-1 ASSOCIATED MYELOPATHY

This application is a Continuation of U.S. application Ser. No. 13/936,290 filed Jul. 8, 2013, which claims the benefit of U.S. Provisional Application No. 61/668,686, filed on Jul. 6, 2012 in the United States Patent and Trademark Office, the disclosures of which are incorporated herein by reference in their entireties.

TECHNICAL FIELD

The present invention relates to a therapeutic method and a therapeutic agent for human T cell leukemia virus type-1 (HTLV-1) associated myelopathy (HAM) patients and asymptomatic HTLV-1 carriers (ACs), which are characterized by reducing HTLV-1 virus-infected cells using an anti-human CC-chemokine receptor 4 (CCR4) antibody.

BACKGROUND ART

Human T cell leukemia virus type-1 (HTLV-1, hereinafter, abbreviated to HTLV-1, also known as human T lymphotropic virus type-1) is a retrovirus that chronically infects human T cells. It has been known that while a majority of HTLV-1-infected patients are asymptomatic and can live their lives in good health, approximately 3-5% of the infected persons develop an active T-cell malignancy called adult T-cell leukemia (ATL, hereinafter, abbreviated to ATL), and another 0.25-3% of the infected persons develop HTLV-1 associated myelopathy (HAM, hereinafter, abbreviated to HAM)/tropical spastic paraparesis (TSP, hereinafter, abbreviated to TSP) (Non-Patent Documents 1-4).

In some cases, HAM/TSP patients develop chronic inflammatory diseases characterized by multi-organ lymphocytic infiltration, including uveitis, arthritis, polymyositis, Sjogren('s) syndrome, infective dermatitis, alveolitis or the like (Non-Patent Document 5).

It has been reported that in $CD4^+$ $CD25^+$ T cells from the peripheral blood of HAM patients, the expression level of forkhead transcription factor (Foxp3) was lower than those from healthy individuals, T cell proliferation regulatory function of $CD4^+$ $CD25^+$ $Foxp3^+$ T cells (regulatory T cells, abbreviated to Treg) is reduced, and deterioration in Treg function is caused by HTLV-1 Tax gene (Non-Patent Document 6).

It has been reported that $CD4^+$ $CD25^+$ CC-chemokine receptor 4 $(CCR4)^+$ Foxp3 high T cells are increased in the peripheral blood of ATL patients, compared to healthy individuals, whereas $CD4^+$ $CD25^+$ $CCR4^+$ Foxp3 low T cells are increased in the peripheral blood of HAM patients, compared to healthy individuals (Patent Document 1, Non-Patent Document 2). It is also reported that there is a correlation between the number of $CD4^+$ $CD25^+$ $CCR4^+$ Foxp3 low T cells in the peripheral blood, the amount of HTLV-1 provirus, and severity of HAM clinical symptoms (Patent Document 1).

Further, it is also reported that in $CD4^+$ $CD25^+$ $CCR4^+$ cells isolated from HAM patients using anti-human CCR4 antibodies the amount of HTLV-1 viral DNA was increased compared to $CD4^+$ $CD25^+$ $CCR4^-$ cells, and interferon-$\gamma$ $(IFN-\gamma)^+$ $CD4^+$ $CD25^+$ Foxp3 low T cell is a pathogenic cell of HAM ($T_{HAM}$), and the cell is increased in the peripheral blood of HAM patients (Patent Document 2, Non-Patent Documents 7, 8).

In the clinical treatment of HAM patients, a therapy with steroids such as prednisolone has been conducted as the treatment of chronic inflammation and a therapy with interferon $\alpha$ has been conducted as the anti-viral therapy.

Meanwhile, CC-chemokine receptor 4 (CCR4) is a seven-transmembrane-type membrane protein that expresses on $CD4^+$ T cells, and thymus and activation-regulated chemokine (TARC)/CCL17 and macrophage-derived chemokine (MDC)/CCL22 are known as its ligands. CCR4 is known to express on Th2, Th17 and Treg cells.

The known anti-human CCR4 antibodies include anti-human CCR4 chimeric antibody (Non-Patent Document 9) and anti-human CCR4 humanized antibody (Non-Patent Document 10). The anti-human CCR4 humanized antibody (general name: Mogamulizumab, product name: Poteligeo®) was approved for the treatment of relapsed and refractory ATL patients.

CITATION LIST

Patent Documents

[PATENT DOCUMENT 1] JP-A 2010-17130
[PATENT DOCUMENT 2] JP-A 2010-100578

Non-Patent Documents

[NON-PATENT DOCUMENT 1] Uchiyama et al, Blood, 1977; 50: 481-492.
[NON-PATENT DOCUMENT 2] Gessain et al, Lancet, 1985; 2: 407-410.
[NON-PATENT DOCUMENT 3] Osame et al, Lancet, 1986; 1; 1031-1032.
[NON-PATENT DOCUMENT 4] Kaplan et al, J. Aquir. Immune Defi. Syndro., 1990; 3: 1096-1101.
[NON-PATENT DOCUMENT 5] Nakagawa et al, J. Neurovirol., 1995; 1: 50-61.
[NON-PATENT DOCUMENT 6] Yamano et al, The Journal of Clinical Investigation, 2005; 115: 1361-1368.
[NON-PATENT DOCUMENT 7] Yamano et al, PLoS One, 2009; 4: e6517.
[NON-PATENT DOCUMENT 8] Araya et al, Viruses, 2011; 3: 1532-1548.
[NON-PATENT DOCUMENT 9] Niwa et al, Cancer Res., 2004; 64: 2127-2133.
[NON-PATENT DOCUMENT 10] Ishii et al, Clin. Cancer Res., 2010; 16: 1520-1531.

SUMMARY OF THE INVENTION

Problems to be Solved by the Invention

As described above, in the clinical treatment of HAM patients, a therapy with a steroid has been conducted as the treatment of chronic inflammation and a therapy with interferon $\alpha$ has been conducted as the anti-viral therapy. However, the effect of these medicaments is insufficient and they cause adverse events such as obesity, diabetes, osteoporosis, glaucoma, infectious diseases, or depression. Therefore, there is a problem that a long term treatment is hardly conducted. At present, functional prognosis of HAM patients is extremely poor, and therefore, there is a strong demand for the development of a new therapeutic method to improve the long term prognosis of patients, which is more effective and has long term tolerability. Accordingly, the object of the present invention is to provide a new therapeutic method and agent for HAM.

Figure 1A:
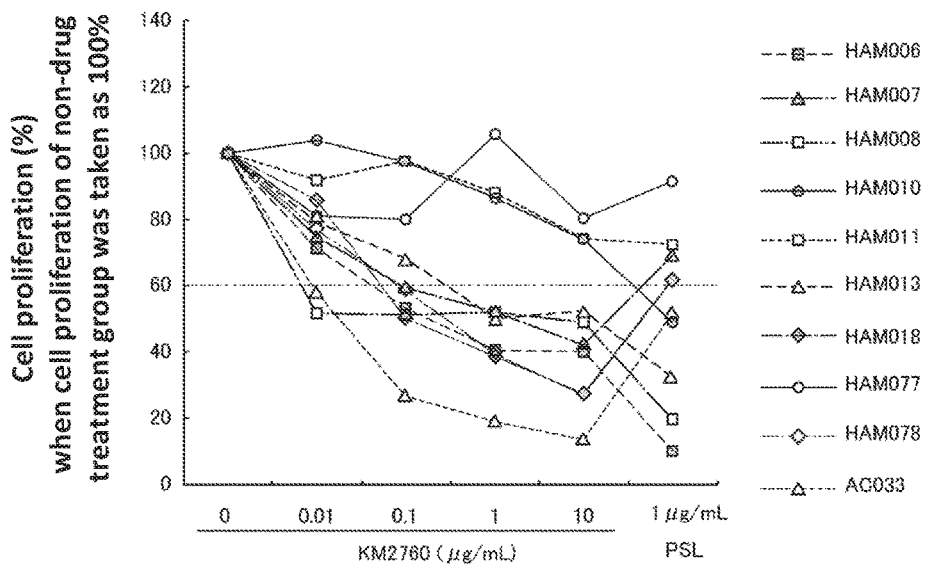
FIG. 1A shows inhibitory effects of anti-human CCR4 chimeric antibody KM2760 and prednisolone on spontaneous cell proliferation of PBMCs derived from HAM patients and asymptomatic HTLV-1 carriers (ACs). The vertical axis represents cell proliferation (%) when cell proliferation of non-drug treatment group was taken as 100%. The horizontal axis represents the concentrations of drugs added. The vertical axis represents cell proliferation ability of sample cells of each patient measured by up-take of $^3$H-thymidine.

The present inventors have found that anti-human CCR4 antibody reduces the HTLV-1 virus-infected cells of HAM patients and ACs, and have completed the present invention. That is, the present invention relates to (1) to (13) below.

(1) A therapeutic method, comprising reducing HTLV-1 virus-infected cells in human T cell leukemia virus type-1 (HTLV-1, hereinafter, abbreviated to HTLV-1, also known as human T lymphotropic virus type-1) associated myelopathy (HAM, hereinafter, abbreviated to HAM) patients and asymptomatic HTLV-1 carriers (AC, hereinafter, abbreviated to AC) using an anti-human CC-chemokine receptor 4 (CCR4) antibody.

(2) The therapeutic method described in (1) above, comprising reducing the amount of HTLV-1 proviral DNA in HAM patients.

(3) The therapeutic method described in (1) or (2) above, comprising reducing cell proliferation of HTLV-1 virus-infected cell.

(4) The therapeutic method described in any one of (1) to (3) above, wherein the HTLV-1 virus-infected cell is CCR4$^+$ T cell.

(5) The therapeutic method described in any one of (1) to (4) above, comprising reducing the expression level of a cytokine produced by the HTLV-1 virus-infected cell.

(6) The therapeutic method described in (5) above, wherein the cytokine is any one selected from interferon γ (IFN-γ), tumor necrosis factor α (TNF-α), interleukin (IL)-2 (IL-2), IL-6, IL-10 and IL-17.

(7) The therapeutic method described in any one of (1) to (6) above, comprising combination treatment with one or more of immunosuppressants and anti-viral agents.

(8) The therapeutic method described in (7) above, wherein the immunosuppressant is any one selected from prednisolone, methylprednisolone, dexamethasone, betamethasone, azathioprine, cyclosporine, tacrolimus, JAK inhibitor, and NFκB inhibitor.

(9) The therapeutic method described in any one of (1) to (8) above, comprising combination treatment with a low dose of immunosuppressant.

(10) A therapeutic agent for HAM patients and ACs comprising an anti-human CCR4 antibody as an active ingredient, wherein the therapeutic agent reduces HTLV-1 virus-infected cells.

(11) A therapeutic agent for HAM patients and ACs comprising an anti-human CCR4 antibody and adrenocorticosteroid as active ingredients, wherein the therapeutic agent reduces HTLV-1 virus-infected cells.

(12) A therapeutic agent for HAM patients and ACs comprising an anti-human CCR4 antibody and adrenocorticosteroid as active ingredients, wherein a low dose of adrenocorticosteroid is used for a long period of time, simultaneously or continuously.

(13) A method selected from the following (i)-(iv) using an anti-human CCR4 antibody:

(i) A method for reducing HTLV-1 virus-infected cells of HAM patients and ACs;

(ii) A method for reducing cell proliferation of HTLV-1 virus-infected cells of HAM patients and ACs;

(iii) A method for reducing HTLV-1 proviral DNA amount of HAM patients and ACs; and (iv) A method for inhibiting production of a cytokine that is produced by HTLV-1 virus-infected cells of HAM patients using anti-human CCR4 antibody.

According to the present invention, a therapeutic method for HTLV-1 associated myelopathy (HAM), comprising reducing HTLV-1 virus-infected cells using an anti-human CCR4 antibody; a therapeutic method for HAM, comprising reducing the amount of HTLV-1 proviral DNA using the anti-human CCR4 antibody; a therapeutic agent for HAM comprising the anti-human CCR4 antibody, which is characterized by reducing HTLV-1 virus-infected cells; and a therapeutic agent for HAM comprising the anti-human CCR4 antibody, which is characterized by reducing the amount of HTLV-1 proviral DNA can be provided.

The therapeutic method and the therapeutic agent of the present invention can inhibit spontaneous cell proliferation ability of peripheral blood mononuclear cells (PBMCs) of HAM patients and ACs, and actual spontaneous cell proliferation to reduce the actual number of cells by using an anti-human CCR4 antibody.

Further, the therapeutic method and the therapeutic agent of the present invention can reduce HTLV-1 virus-infected cells in HAM patients and ACs by using an anti-human CCR4 antibody to reduce the amount of HTLV-1 proviral DNA per cell in PBMC. Therefore, the therapeutic method and the therapeutic agent enable a treatment of HAM patients, and are also useful for asymptomatic HTLV-1 carriers in terms of active treatment and prevention before the onset of HAM.

Furthermore, the therapeutic method and the therapeutic agent of the present invention can inhibit production of inflammatory cytokines in PBMCs of HAM patients, inhibit CD4$^+$ CD25$^+$ CCR4$^+$ Foxp3lowIFN-γ$^+$ T cells ($T_{HAM}$), and also inhibit proliferation of Tax-specific CD8$^+$ T cells to suppress a chronic inflammation, by using an anti-human CCR4 antibody.

The therapeutic method and the therapeutic agent of the present invention reduce the amount of HTLV-1 proviral DNA in the spinal cord region of HAM patients where a chronic inflammation is caused by using an anti-human CCR4 antibody. As a result, the infection rate of spinal fluid cells is decreased, and the production of IFN-γ as a Th1 cytokine is inhibited, and thereby, cellular cytotoxicity immune reactions can be suppressed.

Additionally, the therapeutic method and the therapeutic agent of the present invention can be used in combination with a low dose of steroid agent. The combination treatment can inhibit the production of IFN-γ, TNF-α, and IL-2 as Th1 cytokines more effectively, inhibit $T_{HAM}$ which is a pathogenic cell of HAM, and also inhibit the proliferation of Tax-specific CD8$^+$ T cells.

Further, by the combination treatment with a low dose of steroid agent, the production of inflammatory cytokines in PBMC of HAM patients is inhibited, and thereby, more excellent therapeutic effect can be obtained. The use of a low dose of steroid agent has possibility that it can be applied to a longer term therapy using a steroid agent, and can also reduce the expression frequency of adverse events accompanied by the use of steroid agent.

The present invention relates to a therapeutic method comprising reducing HTLV-1 virus-infected cells in HTLV-1 associated myelopathy (hereinafter, abbreviated to HAM) patients and asymptomatic HTLV-1 carriers (hereinafter, abbreviated to ACs in some cases) using an anti-human CCR4 antibody.

Human T cell leukemia virus type-1 (HTLV-1) is a retrovirus that chronically infects human T cells. It has been known that while a majority of HTLV-1-infected patients are asymptomatic and can live their lives in good health, 0.25-3% of the infected persons develop HTLV-1 associated myelopathy (HAM)/tropical spastic paraparesis (TSP).

HAM is a refractory neuron disease having a pathological feature of chronic myelitis which is caused by infiltration of peripheral blood HTLV-1 infected T cells into the spinal cord. The transmission routes for HTLV-1 are known to include vertical transmission from mother to child, and horizontal transmission through blood transfusion and sexual contact. The symptoms of HAM include gait disturbance, dysuria or the like which is caused by disturbances of the pyramidal tract traveling funiculus lateralis of the thoracic spinal cord.

In the present invention, HAM patients and asymptomatic HTLV-1 carriers (hereinafter, also called HTLV-1 inapparent infected persons) are infected with HTLV-1 virus, and anti-HTLV-1 antibody is detected in the peripheral blood or the cerebrospinal fluid (CSF, hereinafter, referred to as solely spinal fluid) compared to the normal healthy persons.

In the present invention, HAM patients are distinguished from asymptomatic HTLV-1 carriers and normal healthy persons, based on the increased anti-HTLV-1 antibody titer, the increased amount of HTLV-1 proviral DNA, the increased amount of HTLV-1 Tax mRNA, and the increased activated CD4+ cells (CD4$^+$ CD25$^+$ T cells) in the peripheral blood or CSF, and the increased neopterin concentration in the spinal fluid due to spinal inflammation, compared to ACs and normal healthy persons.

The severity of HAM patients can be diagnosed by the ratio of HTLV-1 proviral DNA amount in CSF/peripheral blood cells, with reference to the report that there is a correlation between HAM severity and the ratio of HTLV-1 proviral DNA amount in CSF/peripheral blood cells (Matsuura et al, Journal of Neuroimmune Pharmacology, 2010; 5: 310-325).

The severity can be also examined with reference to the report that it is correlated with the amount of HTLV-1 Tax mRNA or the ratio of HTLV-1 Tax mRNA amount/HTLV-1 proviral DNA amount (Yamano et al, Blood, 2002; 99: 88-94).

In the present invention, an asymptomatic HTLV-1 carrier indicates the patient in whom HTLV-1 virus infection is established but a clinical symptom is not observed. The infection of HTLV-1 virus is detected due to the presence of anti-HTLV-1 antibody titer in the peripheral blood.

The HTLV-1 infected cells in the therapeutic method and the therapeutic agent of the present invention may include CD4$^+$ T cells, CCR4$^+$ T cells, CD4$^+$ CD25$^+$ T cells, CD4$^+$ CD25$^+$ Foxp3lowT cells, CD4$^+$ CD25$^+$ CCR4$^+$ T cells, CD4$^+$ CD25$^+$ CCR4$^+$ Foxp3lowT cells, CD4$^+$ CD25$^+$ CCR4$^+$ Foxp3lowIFN-γ$^+$ T cells, CD8$^+$ CCR4$^+$ T cells or the like.

It includes preferably, any one selected from CD4$^+$ CD25$^+$ CCR4$^+$ T cells, CD4$^+$ CD25$^+$ CCR4$^+$ Foxp3lowT cells and CD4$^+$ CD25$^+$ CCR4$^+$ Foxp3lowIFN-γ$^+$ T cells which are CCR4$^+$ T cells, and more preferably CD4$^+$ CD25$^+$ CCR4$^+$ Foxp3lowIFN-γ$^+$ T cells ($T_{HAM}$).

cytotoxic CD8$^+$ T cells which are specified to HTLV-1 transactivator protein Tax, are increased in the peripheral blood of HAM patients, compared to those in asymptomatic HTLV-1 carriers and normal persons, as a result, it causes a chronic inflammation of the HTLV-1 infected tissue (Yamano et al, Blood, 2002; 99: 88-94). For this reason, CD8$^+$ CCR4$^+$ T cells can be target cells of the therapeutic method and the therapeutic agent of the present invention.

The HTLV-1-infected cells targeted by the therapeutic method and the therapeutic agent of the present invention also include CD4$^+$ CD25$^+$ T cells among HTLV-1-infected cells in the peripheral blood of HAM patients (Yamano et al, J. Exp. Med., 2004; 199; 1367-1377).

CD4$^+$ CD25$^+$ T cells are reservoir cells for HTLV-1 in the peripheral blood cells of HTLV-1-infected persons, and HTLV-1 infection of regulatory T cells (hereinafter, abbreviated to Treg) contained in the CD4$^+$ CD25$^+$ T cell fraction and regulated by expression of forkhead transcription factor 3 (Foxp3), results in Tax-dependent decreasing of Foxp3 expression, and reduction or deletion of regulatory functions of T cell (Yamano et al, J. Clin Invest., 2005; 115: 1361-1368). Therefore, CD4$^+$ CD25$^+$ Foxp3lowT cells are also included as the target cells of the therapeutic method and the therapeutic agent of the present invention.

The HTLV-1-infected cells targeted by the therapeutic method and the therapeutic agent of the present invention include CCR4$^+$ T cells and CD4$^+$ CD25$^+$ CCR4$^+$ T cells having an increased amount of HTLV-1 proviral DNA, among HTLV-1-infected cells in the peripheral blood of HAM patients.

Further, CCR4$^+$ T cells, CD4$^+$ CD25$^+$ CCR4$^+$ T cells, and CD4$^+$ CD25$^+$ CCR4$^+$ Foxp3lowT cells are also included as the target cells of the therapeutic method and the therapeutic agent of the present invention, based on the report that Foxp3 expression is reduced, interferon-γ (IFN-γ) expression is increased, and expressions of interleukin (IL)-2, IL-4, IL-10 and IL-17 are reduced specifically in HTLV-1-infected CD4$^+$ CD25$^+$ CCR4$^+$ T cells (Yamano et al, PLoS One, 2009; 4; e6517).

There is a positive correlation between the ratio of CD4$^+$ CD25$^+$ CCR4$^+$ IFN-γ$^+$ T cells in the peripheral blood mononuclear cells (PBMC) of HAM patients and the amount of neopterin related to spinal inflammation of HAM patients or HAM severity. Meanwhile, there is a low correlation between the amount of HTLV-1 proviral DNA in the peripheral blood of HAM patients and the amount of neopterin or HAM severity. Therefore, it can be suggested that HAM severity is more correlated with the increased amount of HTLV-1-infected T cells having functional changes such as increased IFN-γ production than the absolute amount of HTLV-1-infected T cells in the peripheral blood of patients.

Therefore, the HTLV-1-infected cells targeted by the therapeutic method and the therapeutic agent of the present invention can include T cells with the specific phenotype of $CD4^+ CD25^+ CCR4^+$ Foxp3low IFN-γ$^+$, namely, pathogenic cells of HAM (hereinafter, abbreviated to $T_{HAM}$ in some cases) (Araya et al, Viruses, 2011; 3: 1532-1548.).

In the present invention, $CD4^+$, $CD8^+$, $CD25^+$, $CCR4^+$ or IFN-γ$^+$ cells indicate cell populations that show substantially higher fluorescence intensity than that of a negative control antibody in flow cytometric analysis (hereinafter, abbreviated to FCM) using an antibody specifically binds to each molecule.

In detail, in case of cell membrane proteins, the cell can be directly stained with an antibody specific to each antigen molecule, and in case of secretory proteins, the cell can be stained by performing membrane permeation treatment using a proper surfactant or the like, and protein fixation treatment.

In the present invention, Foxp3low cells mean cells having reduced Foxp3 expression. The cells having reduced Foxp3 expression include a cell in which the Foxp3 expression level identical to that of $CD4^+ CD25^+ CD45RO^-$ cells and can be selected by comparing their Foxp3 expression level to that of the cell population. Further, the Foxp3low cells include cells where no substantial expression of Foxp3 is detected.

In the present invention, the above described cell populations can be selected by using the following antibodies solely or in combination with each other.

Anti-CD4 antibody (OKT4; eBioscience, San Diego, Calif.), anti-CD25 antibody (M-A251; BD Biosciences, San Diego, Calif.), anti-human CCR4 antibody (1G1; BD Biosciences), anti-human CCR4 mouse monoclonal antibody (KM2160, Niwa et al, Cancer Res., 2004; 0.64: 2127-2133), anti-Foxp3 antibody (PCH101; eBioscience), and anti-IFN-γ antibody (B27; BD Biosciences).

The therapeutic method of the present invention includes a therapeutic method comprising reducing HTLV-1 infected cells in the peripheral blood or the spinal fluid of HAM patients by in vivo administration of anti-human CCR4 antibody to HAM patients or ACs.

In detail, the therapeutic method of the present invention includes a therapeutic method comprising reducing HTLV-1-infected cells in the peripheral blood or the spinal fluid of HAM patients while inhibiting or eliminating the target cells such as $CD4^+$ T cells, $CCR4^+$ T cells, $CD4^+ CD25^+$ T cells, $CD4^+ CD25^+$ Foxp3low T cells, $CD4^+ CD25^+ CCR4^+$ T cells, $CD4^+ CD25^+ CCR4^+$ Foxp3low T cells, $CD4^+ CD25^+ CCR4^+$ Foxp3lowIFN-γ$^+$ T cells and $CD8^+ CCR4^+$ T cells using the anti-human CCR4 antibody.

In the present invention, the meaning of reducing HTLV-1-infected cells in the peripheral blood or the spinal fluid of HAM patients is as follows. Generally, whereas spontaneous proliferation of PBMCs of normal healthy persons almost didn't spontaneously proliferate in vitro without stimulation of antibody, cytokine, chemicals or the like, PBMCs of HAM patients spontaneously proliferate even without particular stimulation. Therefore, in the present invention, reducing HTLV-1-infected cells in the peripheral blood or the spinal fluid of HAM patients includes reducing the number of HTLV-1-infected cells by inhibiting spontaneous PBMC proliferation of HAM patients using the anti-human CCR4 antibody.

It also includes the reduction in the number of HTLV-1-infected cells due to specific inhibition of HTLV-1-infected cell proliferation by the anti-human CCR4 antibody or due to cytotoxicity or elimination of HTLV-1-infected cells by effector activity of the anti-human CCR4 antibody.

In the present invention, the meaning of inhibiting cell proliferation of HTLV-1-infected cells in the peripheral blood of HAM patients indicates reduction or inhibition of spontaneous PBMC proliferation when PBMCs of HAM patients are treated with the anti-human CCR4 antibody.

The reduction or inhibition of spontaneous cell proliferation can be assayed by measuring cell proliferation ability of PBMC, for example, by up-take of $^3$H-thymidine, propidium iodide (PI) or the like, proliferating cell nuclear antigen (PCNA) staining, Ki-67 staining, and use of a coloring reagent such as tetrazolium salt or the like.

Further, the therapeutic method of the present invention includes a therapeutic method comprising reducing the amount of HTLV-1 proviral DNA in the peripheral blood and the spinal fluid of HAM patients using the anti-human CCR4 antibody.

In the present invention, the meaning of reducing the amount of HTLV-1 proviral DNA in the peripheral blood of HAM patients is as follows. It indicates a reduction in the amount of HTLV-1 proviral DNA included in PBMCs of HAM patients, a reduction of HTLV-1-infected cells themselves in PBMC, a reduction of new infection of cells in PBMCs (reduction of infection rate).

The amount of HTLV-1 proviral DNA can be measured based on the known method (Nagai et al, Journal of Infectious Diseases; 2001; 183; 197-205). That is, the copy number of HTLV-1 proviral DNA in PBMCs can be measured by amplifying the partial fragment of HTLV-1 pX gene using a specific primer and cDNA derived from PBMC of a HAM patient as a template.

Therefore, the present invention includes a therapeutic method comprising reducing cell proliferation of HTLV-1 virus-infected cells.

The therapeutic method of the present invention include a therapeutic method comprising inhibiting cytokine production of PBMC in the peripheral blood and of cells in the spinal fluid of HAM patients using the anti-human CCR4 antibody.

In the present invention, anti-human CCR4 antibody is able to inhibit production of at least one cytokine selected from IFN-γ, tumor necrosis factor-α (TNF-α), interleukin-2 (IL-2), IL-6, IL-10 and IL-17 that are produced by PBMCs and by cells in the spinal fluid of HAM patients.

In the present invention, the meaning of inhibiting cytokine production of HTLV-1-infected cells in the peripheral blood of HAM patients indicates suppression or inhibition of cytokine production by treatment of PBMCs of HAM patients with the anti-human CCR4 antibody.

Whether cytokine production is inhibited can be confirmed by measuring a cytokine concentration in the plasma or serum collected from HAM patients, or by measuring the cytokine concentration in a culture supernatant that is produced during spontaneous cell proliferation of PBMCs collected from the peripheral blood of HAM patients.

The concentration of cytokine can be measured by enzyme-linked immunosorbent assay (ELISA) method, sandwich-ELISA method, radioimmuno assay (RIA)

method, flow cytometer (FCM) or the like, in which an antibody specific to each cytokine is used. Specifically, the concentration of cytokine can be measured by using a BD™ Cytometric Bead Array (CBA) kit (BD Biosciences).

The anti-human CCR4 antibody used in the present invention and the anti-human CCR4 antibody included in the therapeutic agent of the present invention include any anti-human CCR4 antibody and an antibody fragment thereof, as long as it specifically binds to CCR4, and preferably, an antibody that specifically binds to the extracellular region of CCR4, an antibody that inhibits binding of TARC/CCL17 or MDC/CCL22 to CCR4, an antibody having an effector activity, an antibody that binds to the extracellular region of CCR4 and has an effector activity, an antibody that binds to the extracellular region of CCR4 but does not bind to a platelet, an antibody that binds to the extracellular region of CCR4, does not bind to a platelet, and has an effector activity, or the like.

Human CCR4 is a G protein coupled seven transmembrane receptor cloned as K5-5 from a human immature basophilic cell line KU-812, and has an amino acid sequence represented by SEQ ID NO. 9. The extracellular regions of CCR4 are positions 1-39, positions 99-111, positions 176-206, and positions 268-284 in the amino acid sequence, and the intracellular regions are positions 68-77, positions 134-150, positions 227-242, and positions 309-360 in the amino acid sequence (UniProtKB/Swiss-Prot, ID: P51679).

It is known that TARC (thymus and activation-regulated chemokine) produced from the thymus cells (J. Biol. Chem., 271, 21514, 1996) and MDC (macrophage-derived chemokine) isolated from macrophage (J. Exp. Med., 185, 1595, 1997), also known as STCP-1 (stimulated T cell chemotactic protein-1) (J. Biol. Chem., 272, 25229, 1997) specifically bind to CCR4.

Therefore, the anti-human CCR4 antibody used in the present invention includes an antibody that binds to an epitope included in the extracellular region at positions 1-39, positions 99-111, positions 176-206, and positions 268-284 in the amino acid sequence of CCR4 protein, preferably an antibody that binds to an epitope included in the amino acid sequence at positions 1-39 of the N-terminus of CCR4 protein, and more preferably an antibody that binds to an epitope included in the amino acid sequence at positions 2-29 of CCR4 protein.

The anti-human CCR4 antibody used in the present invention includes any one of monoclonal antibody and polyclonal antibody, and preferably a monoclonal antibody that binds to a single epitope.

The monoclonal antibody includes any one of a monoclonal antibody produced from a hybridoma and a recombinant antibody produced by a genetic recombination technique.

Human chimeric antibody (hereinafter, also called chimeric antibody), humanized antibody [also called human complementarity determining region (CDR)-grafted antibody], and human antibody are preferably used in order to reduce immunogenicity in human.

The chimeric antibody is an antibody composed of a heavy chain variable region (hereinafter, abbreviated to VH) and a light chain variable region (hereinafter, abbreviated to VL) of an antibody of non-human animal, and a heavy chain constant region (hereinafter, abbreviated to CH) and a light chain constant region (hereinafter, abbreviated to CL) of a human antibody. The type of animal for the variable region is not particularly limited, as long as the animal can be used for creating a hybridoma, such as mouse, rat, hamster, rabbit or the like.

The human chimeric antibody can be prepared by obtaining cDNAs encoding VH and VL of an antibody of non-human animal that specifically binds to human CCR4, inserting the cDNAs into an expression vector having genes encoding CH and CL of a human antibody so as to construct a human chimeric antibody expression vector, and introducing the vector into animal cells for expression.

CH of the human chimeric antibody is not particularly limited, as long as it belongs to the human immunoglobulin (hereinafter, abbreviated to hIg), and preferably that of hIgG class. CL of the human chimeric antibody is not particularly limited, as long as it belongs to hIg.

The humanized antibody is an antibody that is prepared by grafting of the complementarity determining region (hereinafter, abbreviated to CDR) of VH and VL of an antibody of non-human animal into the proper site of VH and VL of human antibody. The human CDR-grafted antibody can be prepared by constructing cDNAs encoding variable regions (hereinafter, abbreviated to V regions) where CDRs of VH and VL of an antibody of non-human animal, which specifically binds to CCR4, is grafted into the frameworks (hereinafter, abbreviated to FR) of VH and VL of an arbitrary human antibody, inserting the cDNAs into an expression vector having DNAs encoding CH and CL of human antibody to construct a humanized antibody expression vector, and then introducing the expression vector into an animal cell for expression. The amino acid sequences of the FR of VH and VL of human antibody are not particularly limited, as long as they are derived from human antibody.

CH of the humanized antibody is not particularly limited, as long as it belongs to hIg, and preferably that of hIgG class. CL of the humanized antibody is not particularly limited, as long as it belongs to hIg.

The anti-human CCR4 antibody fragment included in the therapeutic agent of the present invention includes fragments of the antibodies above. The type of the antibody fragment is not particularly limited, and examples thereof include Fab, Fab', F(ab')$_2$, scFv, diabody, dsFv, CDR-containing peptides or the like.

The Fab is an antibody fragment having a molecular weight of about 50,000 and an antigen binding activity, among fragments obtained by treating IgG with papain. The Fab of anti-human CCR4 antibody can be prepared by treating the anti-human CCR4 antibody with papain or by inserting DNA encoding Fab of the antibody into an expression vector, and introducing the vector into a prokaryote or eukaryote to express the Fab.

The F(ab')$_2$ is an antibody fragment having a molecular weight of about 100,000 and an antigen binding activity, among fragments obtained by treating IgG with pepsin (protease). The F(ab')$_2$ of anti-human CCR4 antibody can be prepared by treating anti-human CCR4 antibody with pepsin or by binding Fab' (described below) via a thioether bond or a disulfide bond.

The Fab' is an antibody fragment having a molecular weight of about 50,000 and an antigen binding activity, which is obtained by cutting a disulfide bond of the hinge region of the F(ab')$_2$. The Fab' of anti-human CCR4 antibody can be prepared by treating the F(ab')$_2$ of anti-human CCR4 antibody with dithiothreitol, or by inserting DNA encoding an Fab' of the antibody into an expression vector, and introducing the vector into a prokaryote or eukaryote to express the Fab'.

The scFv is an antibody fragment having an antigen binding activity, which is obtained by linking one VH and one VL using an appropriate peptide linker. The scFv of anti-human CCR4 antibody can be prepared by obtaining cDNAs encoding VH and VL of anti-human CCR4 antibody, constructing DNA encoding scFv, inserting the DNA into an expression vector, and then introducing the expression vector into a prokaryote or eukaryote to express the scFv.

The diabody is an antibody fragment in which scFv forms a dimer, and has a divalent antigen binding activity. The diabody of anti-human CCR4 antibody can be prepared by obtaining cDNAs encoding VH and VL of anti-human CCR4 antibody, constructing DNA encoding the diabody, inserting the DNA into an expression vector, and then introducing the expression vector into a prokaryote or eukaryote to express the diabody.

The dsFv is an antibody fragment obtained by binding polypeptides, in which one amino acid residue of each of VH and VL is substituted with a cysteine residue, via a disulfide bond between the cysteine residues. The dsFv of anti-human CCR4 antibody can be prepared by obtaining cDNAs encoding VH and VL of anti-human CCR4 antibody, constructing DNA encoding dsFv, inserting the DNA into an expression vector, and then introducing the expression vector into a prokaryote or eukaryote to express the dsFv.

The CDR-containing peptide is a peptide containing at least one region of CDRs of VH or VL. The peptide containing CDR of anti-human CCR4 antibody can be prepared by obtaining DNA encoding CDR of VH and VL of anti-human CCR4 antibody, inserting the DNA into an expression vector, and then introducing the expression vector into a prokaryote or eukaryote to express the peptide. Also, the peptide containing CDR of anti-human CCR4 antibody can be prepared by a chemical synthesis method such as an Fmoc method (fluorenylmethyloxycarbonyl method), t-butyloxycarbonyl method, or the like.

In the present invention, the effector activity refers to an activity caused through the Fc region of antibodies, and antibody-dependent cellular cytotoxicity activity (ADCC activity), complement-dependent cytotoxicity activity (CDC activity), or antibody-dependent phagocytosis (ADP activity) by phagocytes such as macrophages or dendritic cells is known.

The known methods of controlling the effector activity are a method for controlling an amount of fucose (also referred to as "core fucose") which is bound to N-acetylglucosamine (GlcNAc) through al-6 bond in a reducing end of a complex type N-linked sugar chain which is bound to asparagine (Asn) at position 297 according to the EU index (Kabat et al, Sequence of Proteins of immunological interests, 5th edition, 1991) in an Fc region of an antibody (WO2005/035586, WO2002/31140, WO00/61739), a method for controlling the effector activity by modifying amino acid residues of the Fc region of the antibody, or the like.

The effector activity of the antibody can be increased or reduced by controlling the amount of core fucose in a complex type N-linked sugar chain which is bound to the Fc region of the antibody. As a method for reducing the content of fucose which is bound to a complex type N-linked sugar chain bound to Fc of the antibody, an antibody to which fucose is not bound can be obtained by the expression of an antibody using a CHO cell which is deficient in α1,6-fucosyltransferase gene (FUT8).

The antibody to which fucose is not bound has a high ADCC activity. On the other hand, as a method for increasing the content of fucose which is bound to a complex type N-linked sugar chain bound to Fc of the antibody, an antibody to which fucose is bound can be obtained by the expression of an antibody using a host cell into which α1,6-fucosyltransferase gene is introduced. The antibody to which fucose is bound has a lower ADCC activity than the antibody to which fucose is not bound.

Further, by modifying amino acid residue(s) in the Fc region of the antibody, the ADCC activity or CDC activity can be increased or decreased. Modification of amino acid residue(s) in the Fc region is performed to increase or decrease the binding activity for FcγR, thereby controlling the ADCC activity. Modification of amino acid residue(s) in the Fc region is performed to increase or decrease binding activity of the complement, thereby controlling the CDC activity.

For example, the CDC activity of the antibody can be increased by using the amino acid sequence of the Fc region described in the specification of US2007/0148165. Further, the ADCC activity or CDC activity can be increased or decreased by modifying the amino acid residues as described in the specifications of U.S. Pat. Nos. 6,737,056, 7,297,775, 7,317,091 and WO2005/070963.

The anti-human CCR4 antibody used in the therapeutic method and the therapeutic agent of the present invention include an anti-human CCR4 antibody that binds to an epitope included at positions 2-29 from the N-terminus of CCR4 protein, an anti-human CCR4 antibody that binds to this epitope to have an ADCC activity, an anti-human CCR4 antibody that includes heavy chain (H chain) CDRs 1-3 containing the amino acid sequences represented by each of SEQ ID NOs. 1-3 and light chain (L chain) CDRs 1-3 containing the amino acid sequences represented by each of SEQ ID NOs. 4-6, and an anti-human CCR4 antibody that includes VH containing the amino acid sequence represented by SEQ ID NO. 7 and VL containing the amino acid sequence represented by SEQ ID NO. 8. Further, an antibody, in which core fucose bound at position 297 of Fc of the above described antibody is reduced or deleted, is preferred. More particularly, an anti-human CCR4 humanized antibody (Poteligeo®, general name: Mogamulizumab) can be exemplified.

The therapeutic method of the present invention includes a combination therapy by combining the anti-human CCR4 antibody and other therapeutic agents.

In the combination therapy of the present invention, the anti-human CCR4 antibody can be used in combination with at least one combination drug selected from immunosuppressants and anti-viral agents. In the combination therapy of the present invention, the combination drug and the anti-human CCR4 antibody can be administrated simultaneously or continuously.

The immunosuppressants include adrenocorticosteroid drugs such as prednisolone, methylprednisolone, dexamethasone, betamethasone or the like, antimetabolites such as azathioprine or the like, calcineurin inhibitors such as cyclosporine, tacrolimus (FK-506) or the like, Janus kinase (JAK) inhibitors such as tofacitinib, tasocitinib or the like, CTLA4-Ig drugs prepared by fusion of cytotoxic T lymphocyte associated antigen-4 (CTLA-4) with antibody Fc region, such as abatacept, NFκB inhibitors or the like, which are drugs capable of suppressing excessive immune reactions of HAM. Further, derivatives of the drugs described above that acts in the same manner on the molecular targeted by each drug can also be used.

The anti-viral agents include anti-viral cytokines such as IFN-α or the like, reverse transcriptase inhibitors such as azidothymidine or the like.

10-60 mg of prednisolone are typically used for chronic inflammation symptoms of HAM patients. However, because long-term administration of prednisolone causes adverse effects such as obesity, diabetes, osteoporosis, glaucoma, infectious diseases or the like, it is necessary to control the administration amount according to the inflammation symptoms of HAM patients.

The combination therapy of the present invention exerts stronger anti-inflammatory effects by using the anti-human CCR4 antibody in combination with a relatively low dose of adrenocorticosteroid. Therefore, the combination therapy of the present invention includes a therapeutic method of using the anti-human CCR4 antibody in combination with the low dose of adrenocorticosteroid simultaneously or continuously. By using the anti-human CCR4 antibody, the long-term use of the low dose of adrenocorticosteroid is also included. Further, it includes a therapeutic method of using the anti-human CCR4 antibody in combination with the low dose of adrenocorticosteroid simultaneously or continuously which is characterized by reducing or preventing the onset of adverse events accompanied by the long-term use of adrenocorticosteroid drug by the combination therapy of the present invention. In the combination therapy of the present invention, the anti-human CCR4 antibody and the adrenocorticosteroid can be administrated simultaneously or continuously.

In the present invention, the low dose of adrenocorticosteroid is exemplified as, for example, 1-10 mg of prednisolone, and preferably 9 mg, 8 mg, 7 mg, 6 mg, 5 mg, 4 mg, 3 mg, 2 mg and 1 mg thereof.

Further, the therapeutic agent for HAM patients and ACs of the present invention may include a therapeutic agent for HAM patients and ACs comprising the anti-human CCR4 antibody, which is characterized by reducing HTLV-1-infected cells in the peripheral blood and spinal fluid of HAM patients, a therapeutic agent for HAM patients and ACs comprising the anti-human CCR4 antibody, which is characterized by reducing the amount of HTLV-1 proviral DNA in the peripheral blood and spinal fluid of HAM patients, and a therapeutic agent for HAM patients and ACs comprising the anti-human CCR4 antibody, which is characterized by targeting at least one cell selected from $CD4^+$ T cells, $CD4^+$ $CD25^+$ T cells and $CD8^+$ T cells present in the peripheral blood and spinal fluid of HAM patients The therapeutic agent for HAM patients and ACs of the present invention include any one, as long as it is a therapeutic agent comprising the anti-human CCR4 antibody with the above described activity as an active ingredient, and it is preferably provided as a drug formulation that is typically prepared by mixing with one or more pharmaceutically acceptable carriers according to any method well-known in the pharmaceutical fields.

Preferably, an aseptic solution where it is dissolved in an aqueous carrier such as water, or an aqueous solution of salt, glycine, glucose or human albumin is used. It is also possible to add a pharmaceutically acceptable additive such as buffer or tonicity agent for making the preparation solution more similar to the physiological conditions and examples thereof include sodium acetate, sodium chloride, sodium lactate, potassium chloride, sodium citrate or the like. It can be also preserved by freeze-drying and, in actual use, it can be used by dissolving in an appropriate solvent.

With regard to the administration route of the therapeutic agent of the present invention, it is preferred to use the most effective route for the treatment. Examples thereof include oral administration and parenteral administration such as intraoral, tracheobronchial, intrarectal, subcutaneous, intramuscular, intrathecal, and intravenous administrations. Intrathecal or intravenous administration is preferred.

Examples of the preparation suitable for the oral administration may include emulsion, syrup, capsule, tablet, powder, granule or the like. For example, a liquid preparation such as emulsion and syrup can be prepared using water, saccharides such as sucrose, sorbitol and fructose, glycols such as polyethylene glycol and propylene glycol, oils such as sesame oil, olive oil and soybean oil, antiseptics such as esters of p-hydroxybenzoic acid, flavors such as strawberry flavor and peppermint flavor, or the like as additives.

Capsule, tablet, powder, granule, or the like can be prepared using excipients such as lactose, glucose, sucrose, mannitol or the like, disintegrating agents such as starch, sodium alginate or the like, lubricants such as magnesium stearate, talc or the like, binders such as polyvinyl alcohol, hydroxypropyl cellulose, gelatin or the like, surfactants such as fatty acid ester or the like, plasticizers such as glycerin or the like, as additives.

Examples of the preparation suitable for parenteral administration may include an injectable formulation, suppository, air spray or the like. For example, injectable formulation is prepared using a carrier including a salt solution, a glucose solution or a mixture thereof. Suppository is prepared using a carrier such as cacao butter, hydrogenated fat, carboxylic acid or the like. Air spray is prepared using, for example, a carrier which does not stimulate the antibody itself, and the mouth and the airway mucous membrane of a person to be administered, and which disperses the antibody into fine particles and makes the absorption easy.

Specific examples of the carrier include lactose, glycerin or the like. Depending upon the property of the antibody and the carrier used, it is possible to prepare aerosol, dry powder, or the like. In addition, even in the parenteral preparation, components exemplified as additives in the oral preparation may be added.

The administration dose or frequency of the therapeutic agent of the present invention varies depending on desired therapeutic effect, administering method, period for the treatment, age, body weight or the like and, usually, it is 1 µg/kg-10 mg/kg per day for an adult.

Further, the therapeutic agent for HAM patients and ACs of the present invention includes a therapeutic agent for HAM comprising the anti-human CCR4 antibody and a low dose of adrenocorticosteroid, and a therapeutic agent for HAM comprising the anti-human CCR4 antibody and adrenocorticosteroid, which is characterized by using it in combination with the low dose of adrenocorticosteroid, a therapeutic agent for HAM comprising the anti-human CCR4 antibody and adrenocorticosteroid, which is characterized by using it in combination with the low dose of adrenocorticosteroid simultaneously or sequentially, a therapeutic agent comprising the anti-human CCR4 antibody and a low dose of adrenocorticosteroid, which is characterized by using the low dose of adrenocorticosteroid for a long period of time, a therapeutic agent comprising the anti-human CCR4 antibody and the low dose of adrenocorticosteroid, which is characterized by using the low dose of adrenocorticosteroid simultaneously or sequentially for a long period of time.

The therapeutic method for HAM using the anti-human CCR4 antibody and the therapeutic agent for HAM comprising the anti-human CCR4 antibody of the present invention can be applied in the active treatment of asymptomatic HTLV-1 carriers or inactive HAM patients. By the active treatment of AC, the treatment before the onset of the chronic inflammation can be made, and thus nerve damage or tissue damage can be inhibited.

Further, the active treatment of inactive HAM patients inhibits chronic inflammatory reactions to give the patients a recovery period of nerve damage or tissue damage that occurs during a HAM active period, and thus is very important in the improvement of symptoms and quality of life (QOL).

In other words, the present invention also includes a method of lowering the risk of the onset of HAM by reducing the HTLV-1-infected cells in the patient's peripheral blood and spinal fluid, a method of lowering the risk of the onset of HAM by reducing the amount of HTLV-1 proviral DNA in the patient's peripheral blood and spinal fluid, and a method of lowering the risk of the onset of HAM by inhibiting production of cytokines derived from HTLV-1-infected cells in the patient's peripheral blood and spinal fluid; by administrating the anti-human CCR4 antibody, in the HTLV-1 carriers with a high-risk of HAM, who are asymptomatic although the amounts of anti-HTLV-1 antibody and HTLV-1 proviral DNA in the peripheral blood or spinal fluid are detected.

Further, the present invention also includes a preventing agent for HAM comprising the anti-human CCR4 antibody, which is characterized by lowering the risk of the onset of HAM development by reducing the HTLV-1-infected cells in the patient's peripheral blood and spinal fluid in the asymptomatic HTLV-1 carriers with a high-risk of HAM.

The HTLV-1 carriers with a high-risk of the onset of HAM can be distinguished by a diagnostic marker selected from the anti-HTLV-1 antibody titer, the amount of HTLV-1 proviral DNA, the amount of HTLV-1 Tax mRNA, the ratio of HTLV-1 Tax mRNA/HTLV-1 proviral DNA, and the number of $CD4^+$ $CD25^+$ T cells in the peripheral blood or spinal fluid, the neopterin concentration in the spinal fluid, the ratio of HTLV-1 proviral DNA in CSF/PBMC, soluble IL-2 receptor (sIL-2R), CXCL10 concentration, HAM/ATL family history or the like.

With respect to HAM patients, specifically, HAM patients that are recognized to have at least one risk factor selected from a high level of HTLV-1 proviral DNA in the peripheral blood, a high level of serum sIL-2R, a high level of serum CXCL10, HAM/ATL family history, a high level of virus in the spinal fluid, increased HTLV-1 antibody titer, high levels of neopterin and CXCL10 can be a subject of the active treatment. The high level of each diagnostic marker means a relatively high level between HAM patients.

With respect to ACs, specifically, ACs that are recognized to have at least one risk factor selected from a high level of HTLV-1 proviral DNA, a high level of serum sIL-2R, a high level of serum CXCL10, and HAM/ATL family history can be high-risk ACs.

On the contrary, ACs that are recognized to have a risk factor selected from a low level of HTLV-1 proviral DNA, a low level of serum sIL-2R, a low level of serum CXCL10, and no HAM/ATL family history can be low-risk ACs. The high level of each diagnostic marker means a relatively high level between ACs, and includes higher levels than the HAM diagnostic values.

Further, the present invention also includes a method of lowering the HAM severity by reducing the HTLV-1-infected cells in the subject's peripheral blood and spinal fluid, a method of lowering the HAM severity by reducing the amount of HTLV-1 proviral DNA in the subject's peripheral blood and spinal fluid, and a method of lowering the HAM severity by inhibiting production of cytokines derived from HTLV-1-infected cells in the subject's peripheral blood and spinal fluid; by administrating the anti-human CCR4 antibody, in inactive HAM patients with minor motor disturbance.

Furthermore, the present invention includes a method for reducing the HTLV-1-infected cells in the peripheral blood and spinal fluid of HAM patients using the anti-human CCR4 antibody, a method for reducing the amount of HTLV-1 proviral DNA in the peripheral blood and spinal fluid of HAM patients using the anti-human CCR4 antibody, and a method for reducing production of cytokines and/or chemokines in the peripheral blood and spinal fluid of HAM patients using the anti-human CCR4 antibody.

EXAMPLES

Hereinafter, the present invention will be described in detail with reference to Examples, but is not limited to these Examples.

[Example 1] Inhibitory Effect of Anti-Human CCR4 Antibody on Spontaneous PBMC Proliferation of HAM Patients In order to examine the effects of anti-human CCR4 antibody on spontaneous cell proliferation of peripheral blood mononuclear cells (PBMC) in the peripheral blood of HAM patients, anti-human CCR4 chimeric antibody KM2760 (Japanese Patent NO. 3926153) (hereinafter, abbreviated to KM2760) was added to PBMCs isolated from HAM patients, followed by cultivation.

Hereinafter, the peripheral bloods of HAM patients and asymptomatic HTLV-1 carriers used in Examples were the samples obtained from each of the subjects who gave the informed consent, based on the Declaration of Helsinki that is included in the clinical protocol examined and approved by The Ethics Committee of St. Marianna University School of Medicine.

PBMCs of HAM patients and asymptomatic HTLV-1 carriers (AC) were isolated from peripheral bloods that were collected from 9 HAM patients and 8 asymptomatic HTLV-1 carriers by Ficoll density gradient centrifugation, and frozen and stored in liquid nitrogen until assay. The isolated PBMCs were suspended in an RPMI1640 medium containing 10% fetal bovine serum (hereinafter, abbreviated to FBS), 1% penicillin and 1% streptomycin (manufactured by Wako Pure Chemical Industries, Ltd.) (hereinafter, abbreviated to RPMI medium) without proliferation stimulation, and seeded at a density of $1 \times 10^5$ cells/100 μL/well in a 96-well round bottom plate. A well added with 1 μg/mL of prednisolone (PSL) was prepared as a positive control, and wells added with 0-10 μg/mL of anti-human CCR4 chimeric antibody KM2760 were prepared as a subject antibody. Cultivation was performed under the conditions of 37° C. and 5% $CO_2$ for 6 days.

Figure 1B:
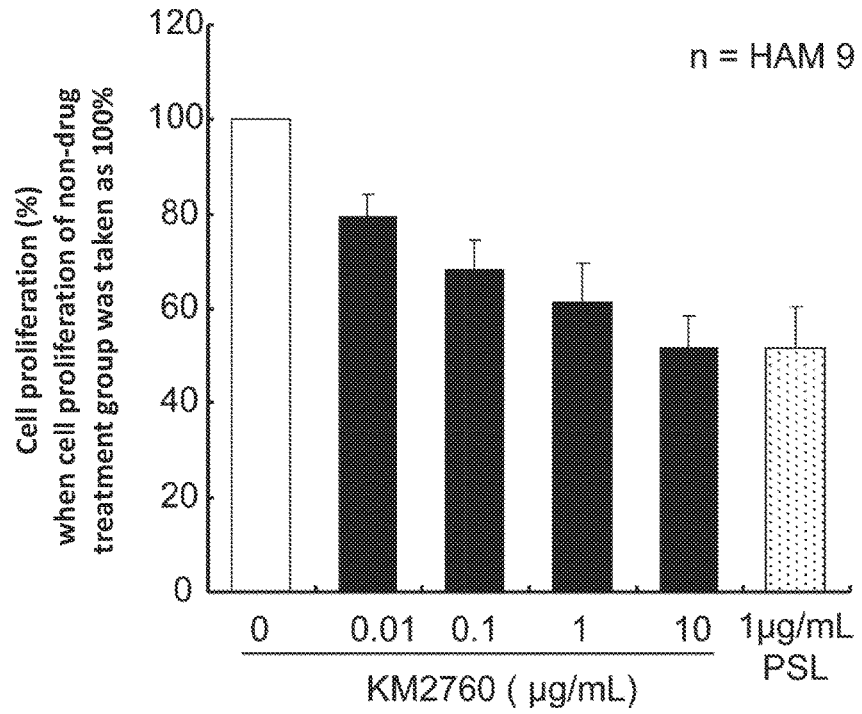
FIG. 1B represents cell proliferation ability of PBMCs of 9 HAM patients of FIG. 1A measured by $^3$H-thymidine up-take. The vertical axis represents cell proliferation (%) when cell proliferation of non-drug treatment group was taken as 100%. The horizontal axis represents drugs added.

After cultivation, 1 μCi $^3$H-thymidine was added to each well, and further cultured for 16 hours. After cultivation, the cells were recovered, and specific radioactivity was measured using a liquid scintillation counter (Micro Beta) to determine cell proliferation rate (%) (FIGS. 1A, 1B). The up-take of $^3$H-thymidine in the non-drug-treated well was taken as 100%, and the ratio was determined.

As a result, PSL of the positive control showed approximately 50% cell proliferation inhibition, compared to non-drug treatment. In contrast, the anti-human CCR4 chimeric antibody KM2760 inhibited cell proliferation in an antibody concentration-dependent manner, 0.01 μg/mL thereof showed approximately 80% cell proliferation inhibition, compared to the control, and 10 μg/mL thereof showed cell proliferation inhibition equivalent to that of PSL (FIG. 1B).

In addition, KM2760 inhibited spontaneous cell proliferation, as in PBMC derived from 1 asymptomatic HTLV-1 carrier (FIG. 1A).

Therefore, it was revealed that the anti-human CCR4 antibody inhibited spontaneous cell proliferation ability of PBMCs derived from HAM patients and asymptomatic HTLV-1 carriers.

Figure 1C:
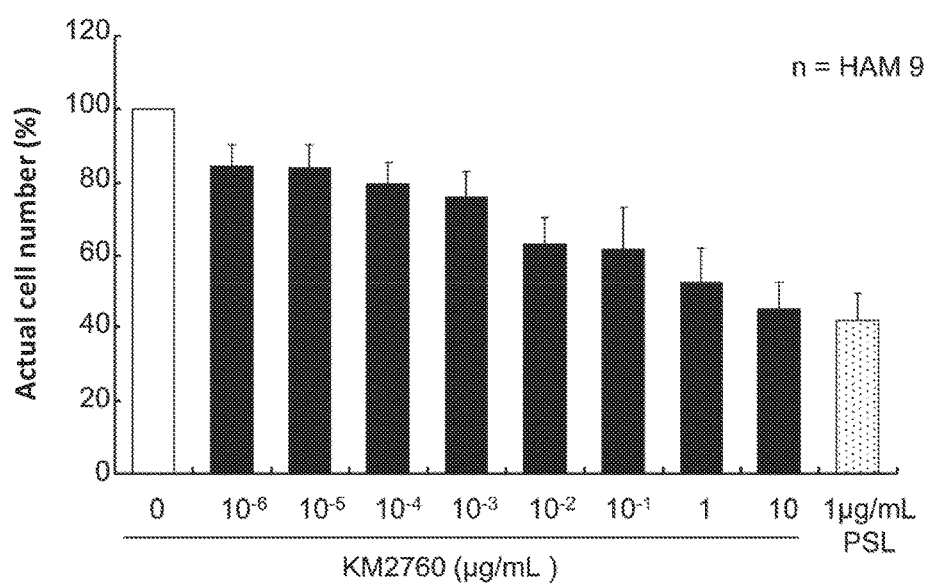
FIG. 1C represents cell proliferation (%) of actual cell number of PBMCs of 9 HAM patients of FIG. 1A. The vertical axis represents actual cell number (%) when actual cell number of non-drug treatment group was taken as 100%. The horizontal axis represents drugs added.

In the same manner, PBMCs derived from HAM patients were cultured by addition of $1\times10^{-6}$ μg/mL-10 μg/mL of KM2760, and at 7 days after cultivation, the actual number of cells was counted (FIG. 1C).

As a result, 1 μg/mL of PSL reduced the number of cells to approximately 50%, compared to that of non-drug treatment. In addition, KM2760 reduced the number of cells in an antibody concentration-dependent manner. In a very low concentration range from 1 pg/mL to 1 ng/mL, the number of cells was reduced to approximately 80%, compared to that of non-drug treatment. 10 μg/mL thereof showed the reduction in the number of cells equivalent to that of 1 μg/mL of PSL.

These results revealed that the anti-human CCR4 chimeric antibody inhibits spontaneous cell proliferation ability of PBMCs of HAM patients and actual spontaneous cell proliferation to reduce the actual number of cells.

[Example 2] Inhibitory Effect of Anti-Human CCR4 Antibody on HTLV-1 Proviral DNA Amount in PBMCs of HAM Patients In order to examine the effects of anti-human CCR4 chimeric antibody KM2760 on the amount of HTLV-1 provirus in PBMCs of HAM patients, PBMCs derived from HAM patients were cultured with addition of KM2760 in the same manner as in Example 1.

The amount of HTLV-1 proviral DNA was quantified in accordance with the method described in Yamano et al (Blood, 2002; 99: 88-94) and Nagai et al (J. Infectious Diseases; 2001; 183: 197-205).

At 7 days after cultivation, cells were recovered from each well, and the recovered cells were suspended in a buffer containing 50 mM Tris-HCl (pH 8.0), 20 mM EDTA, 0.1 M NaCl and 1% SDS (hereinafter, referred to as lysis buffer), and then 150 μg/mL of proteinase K (manufactured by Wako Pure Chemical Industries, Ltd.) was added thereto, followed by shaking at 55° C. overnight. Then, genomic DNAs were extracted from PBMCs of HAM patients using phenol/chloroform.

Real time-polymerase chain reaction (hereinafter, abbreviated to PCR) was performed using the extracted genomic DNA as a template, and TaqMan probes for HTLV-1 pX region and human β-actin, and a primer set of each gene.

As a standard sample of HTLV-1 pX, a genomic DNA derived from HTLV-1 infected rat TARL2 cell line where 1 copy/cell of HTLV-1 pX region was integrated was used, and as a standard sample of β-actin, a genomic DNA derived from PBMC of a normal person was used to perform PCR at the same time and to obtain a standard curve. The copy numbers of pX and β-actin of each sample were calculated using the standard curve, and the amount of HTLV-1 proviral DNA was determined by the following Equation (FIGS. 2A and 2B).

Amount of HTLV-1 proviral DNA: copy number of HTLV-1(pX)/100 PBMC cells=(copy number of pX)/(copy number of β-actin/2)×100

Figure 2A:
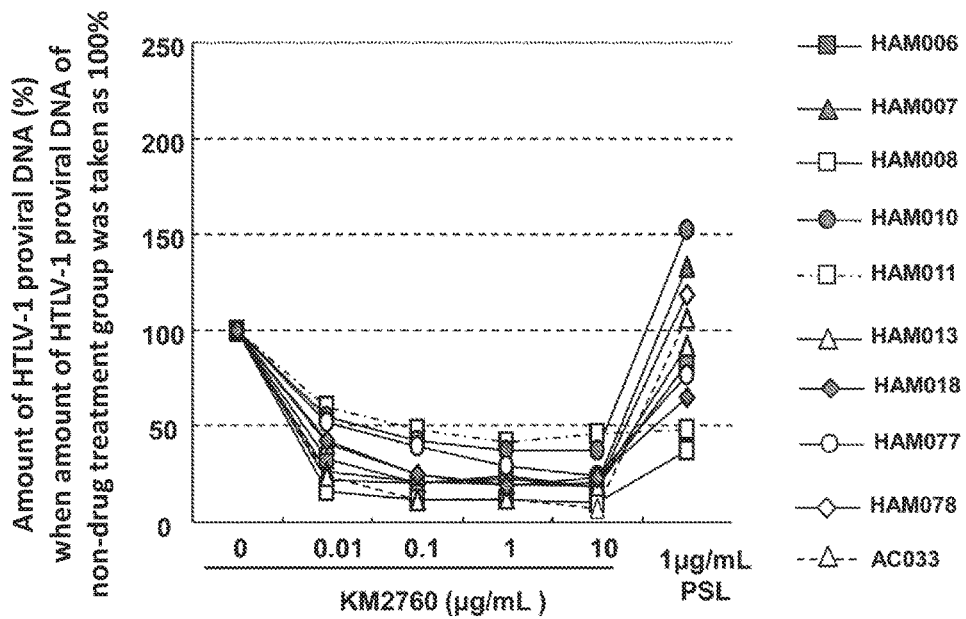
FIG. 2A shows inhibitory effects of anti-human CCR4 chimeric antibody KM2760 and prednisolone on the amount of HTLV-1 proviral DNA in PBMCs derived from 9 HAM patients and an asymptomatic HTLV-1 carrier (AC). The HTLV-1 proviral DNA load was measured by quantitative real-time PCR method. The vertical axis represents the amount of HTLV-1 proviral DNA (%) when the amount of HTLV-1 proviral DNA of non-drug treatment group was taken as 100%, and the horizontal axis represents drugs added. It represents the amount of HTLV-1 proviral DNA of each patient sample. Comparison with non-antibody treatment: Friedman's test with Dunn's post test was performed to test a significant difference.
Figure 2B:
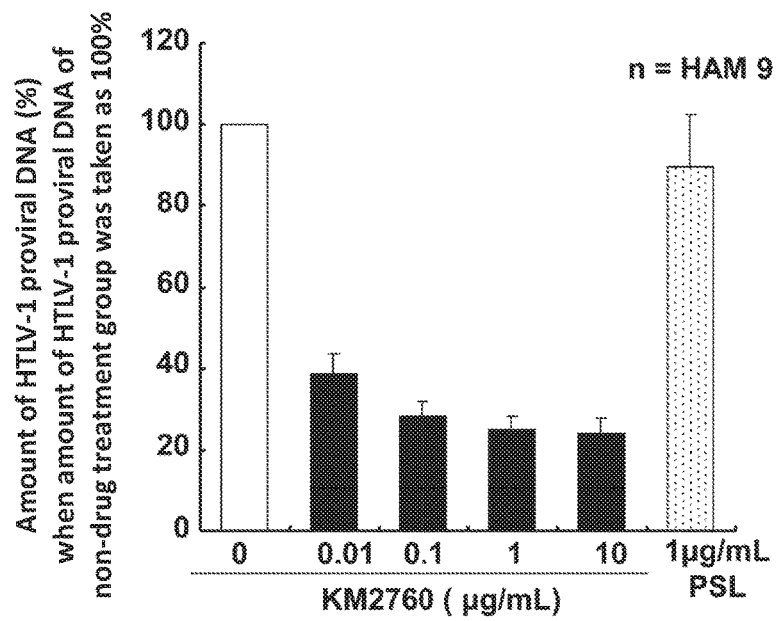
FIG. 2B represents the mean value of HTLV-1 proviral DNA amounts in PBMCs of 9 HAM patients of FIG. 2A. The vertical axis represents the amount of HTLV-1 proviral DNA (%) when the amount of HTLV-1 proviral DNA of non-drug treatment group was taken as 100%, and the horizontal axis represents the concentrations of drugs added. Comparison with non-antibody treatment: Friedman's test with Dunn's post test was performed to test a significant difference.

As a result, 1 μg/mL PSL did not show the effect of reducing the amount of HTLV-1 proviral DNA in PBMCs derived from HAM patients, compared to non-drug treatment, whereas the anti-human CCR4 chimeric antibody KM2760 remarkably reduced the amount of HTLV-1 proviral DNA in an antibody concentration-dependent manner. 0.01 μg/mL of KM2760 reduced the amount of HTLV-1 proviral DNA in PBMCs derived from HAM patients to 40%, and 1 μg/mL-10 μg/mL of KM2760 reduced the amount of HTLV-1 proviral DNA to approximately 30%, compared to non-drug treatment (FIG. 2B).

KM2760 also reduced the amount of HTLV-1 proviral DNA in PBMCs of asymptomatic HTLV-1 carriers, same as in HAM patients (FIG. 2A).

Figure 2C:
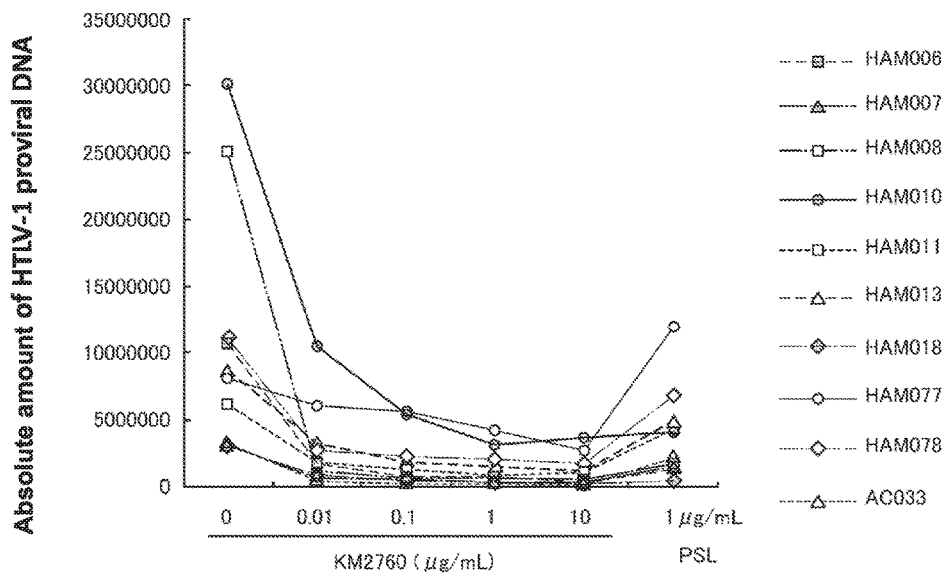
FIG. 2C represents the absolute amount of HTLV-1 proviral DNA of each patient sample of FIG. 2A. The vertical axis represents the amount of HTLV-1 proviral DNA of each sample well, and the horizontal axis represents the concentrations of drugs added. Comparison with non-antibody treatment: Friedman's test with Dunn's post test was performed to test a significant difference.
Figure 2D:
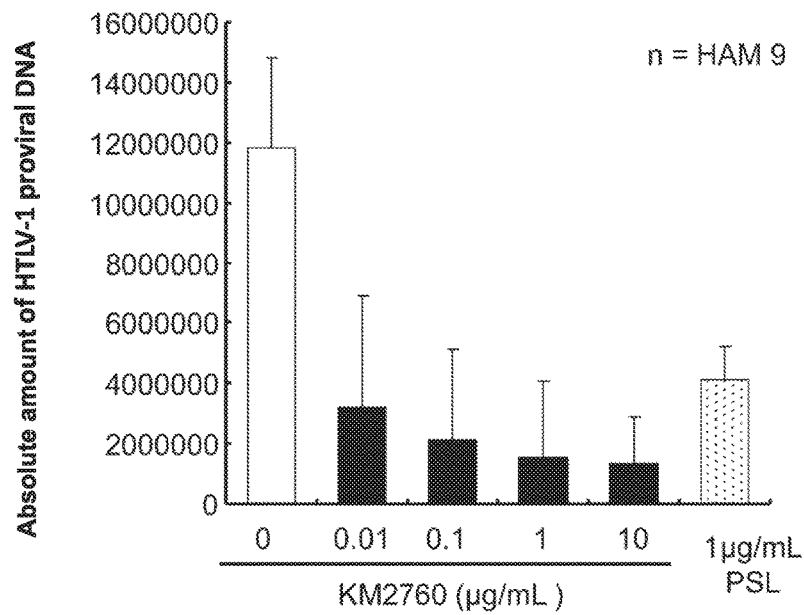
FIG. 2D represents the mean value of absolute HTLV-1 proviral DNA amounts in PBMCs of 9 HAM patients of FIG. 2C. The vertical axis represents the absolute amount of HTLV-1 proviral DNA of each sample well, and the horizontal axis represents drugs added. Comparison with non-antibody treatment: Friedman's test with Dunn's post test was performed to test a significant difference.

Cultivation was performed in the same manner, and the absolute amount of the HTLV-1 proviral DNA per well was determined (FIGS. 2C and 2D). As a result, 1 μg/mL PSL reduced the absolute amount of HTLV-1 proviral DNA in PBMCs derived from HAM patients to ⅓, compared to the well of non-drug treatment, whereas KM2760 reduced the absolute amount of HTLV-1 proviral DNA in an antibody concentration-dependent manner, and 10 μg/mL of KM2760 reduced the absolute amount of HTLV-1 proviral DNA to approximately ⅙.

Figure 2E:
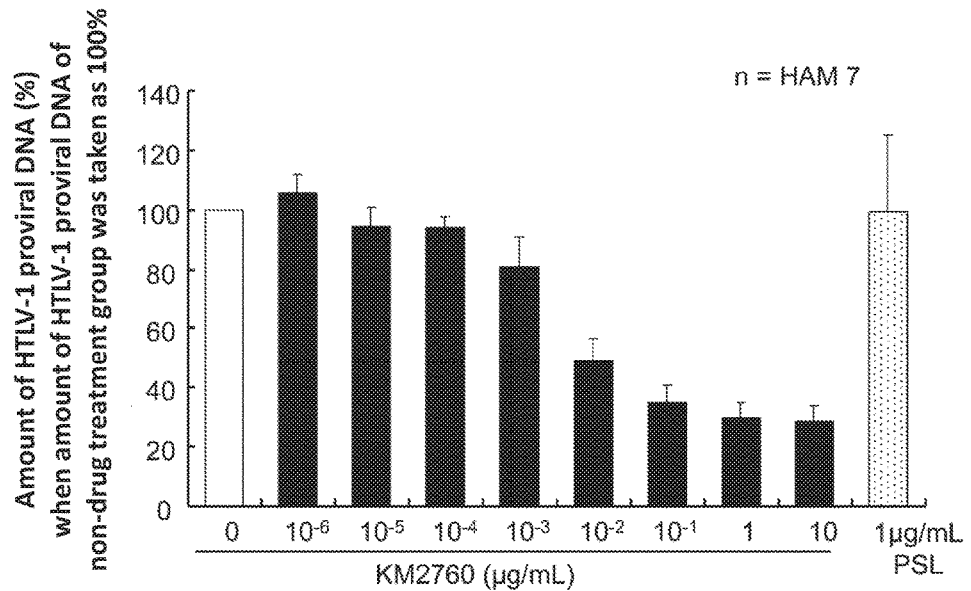
FIG. 2E shows inhibitory effects of anti-human CCR4 chimeric antibody KM2760 and prednisolone on the amount of HTLV-1 proviral DNA in PBMCs derived from HAM patients. The vertical axis represents the amount of HTLV-1 proviral DNA (%) when the amount of HTLV-1 proviral DNA of non-drug treatment group was taken as 100%, and the horizontal axis represents the concentrations of drugs added. It represents the mean value of HTLV-1 proviral DNA amounts in PBMCs of 7 HAM patients. Comparison with non-antibody treatment: Friedman's test with Dunn's post test was performed to test a significant difference.

In the same manner as above, $1\times10^{-6}$ μg/mL-10 μg/mL of KM2760 were added to culture PBMCs derived from HAM patients, and at 7 days after cultivation, the amounts of HTLV-1 proviral DNA were determined (FIG. 2E).

As a result, 1 μg/mL of PSL almost didn't reduce the amount of proviral DNA, but 0.01 μg/mL-10 μg/mL of anti-human CCR4 chimeric antibody KM2760 reduced the amount of HTLV-1 proviral DNA to 50%-30%, compared to non-drug treatment.

Figure 2F:
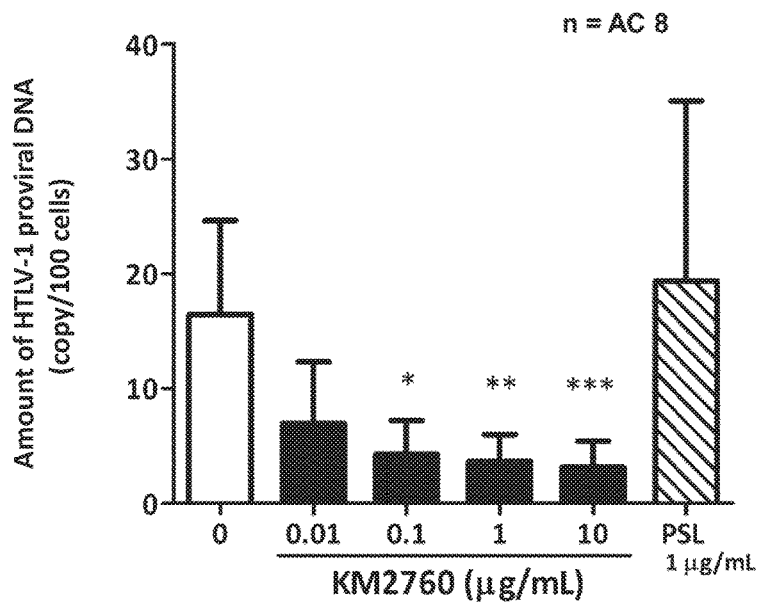
FIG. 2F shows inhibitory effects of anti-human CCR4 chimeric antibody KM2760 and prednisolone on the amount of HTLV-1 proviral DNA in PBMCs derived from 8 asymptomatic HTLV-1 carriers (ACs). The vertical axis represents the amount of proviral DNA (copy/100 cells), and the horizontal axis represents the concentrations of drugs added. Comparison with non-antibody treatment: Friedman's test with Dunn's post test was performed to test a significant difference.

On the other hand, with respect to the asymptomatic HTLV-1 carrier (AC), $1\times10^{-2}$ μg/mL-10 μg/mL of KM2760 were added to culture PBMCs derived from AC (N=8) in the same manner as above, and at 7 days after cultivation, the amounts of HTLV-1 proviral DNA were determined (FIG. 2F).

As a result, 1 μg/mL of PSL almost didn't reduce the amount of proviral DNA, but 0.01 μg/mL-10 μg/mL of anti-human CCR4 chimeric antibody KM2760 reduced the amount of HTLV-1 proviral DNA to ¼-⅕, compared to non-drug treatment.

These results revealed that the anti-human CCR4 chimeric antibody inhibits cell proliferation of PBMCs of HAM patient and AC, and also reduces the amount of HTLV-1 proviral DNA per cell and further the absolute amount of HTLV-1 provirus DNA in PBMCs. In addition, it was also suggested that its inhibitory effect on the amount of HTLV-1 proviral DNA was significantly higher than that of 1 μg/mL of PSL.

Accordingly, it was shown that the anti-human CCR4 antibody reduces the HTLV-1-infected cells of HAM patient and AC, and also reduces the HTLV-1 infection rate. This indicates that the anti-human CCR4 antibody is able to treat HAM patients by reducing the HTLV-1-infected cells and the amount of HTLV-1 proviral DNA, and also indicates on asymptomatic HTLV-1 carrier in the same way so as to be effective for the active treatment or prevention prior to the onset of HAM.

[Example 3] Combination Effect of Anti-Human CCR4 Antibody

Referring to the results that the anti-human CCR4 antibody has the inhibitory effect on cell proliferation of PBMCs derived from HAM patients and the effect of reducing the amount of HTLV-1 proviral DNA, its combination effect with adrenocorticosteroid drugs clinically used was examined.

Usually, after oral administration of 50 mg of prednisolone to a clinical patient, its blood concentration is approximately 1 μg/mL, and after oral administration of a low dose of 5 mg of prednisolone to a clinical patient, its blood concentration is approximately 0.1 μg/mL. In this experiment, therefore, oral administration of a low dose of prednisolone was considered, and combination effect with 0.1 μg/mL of prednisolone was examined.

In the same manner as in Example 1, PBMCs isolated from the peripheral blood of HAM patient were seeded in a 96-well bottom plate. A well added with 0.1 or 1 μg/mL of prednisolone and wells added with 0.1 μg/mL prednisolone+ 0.01-10 μg/mL of anti-human CCR4 chimeric antibody KM2760 were prepared to perform cultivation.

For cell proliferation assay by $^3$H-thymidine up-take, $^3$H-thymidine was added at 6 days after cultivation in the same manner as in Example 1, and further cultured for 16 hours. Further, the amount of HTLV-1 proviral DNA was determined at 7 days after cultivation in the same manner as in Example 2.

In all assays, the proliferation rate (FIGS. 3A and 3B) or the amount of HTLV-1 proviral DNA (FIGS. 3C and 3D) was represented as a percentage, when the well treated with no drug was taken as 100%.

As a result, 0.1 or 1 μg/mL of prednisolone inhibited cell proliferation to approximately 70% or 50%, compared to non-drug treatment. Further, addition of 0.1 μg/mL PSL with KM2760 inhibited cell proliferation in an antibody concentration-dependent manner, compared to non-drug treatment, and 0.1 μg/mL PSL+10 μg/mL KM2760 inhibited cell proliferation to 20%, compared to non-drug treatment (FIGS. 3A and 3B).

Therefore, it was revealed that the PBMC cell proliferation of HAM patients was more strongly inhibited by combination treatment of the low dose of PSL with anti-human CCR4 antibody.

Figure 3A:
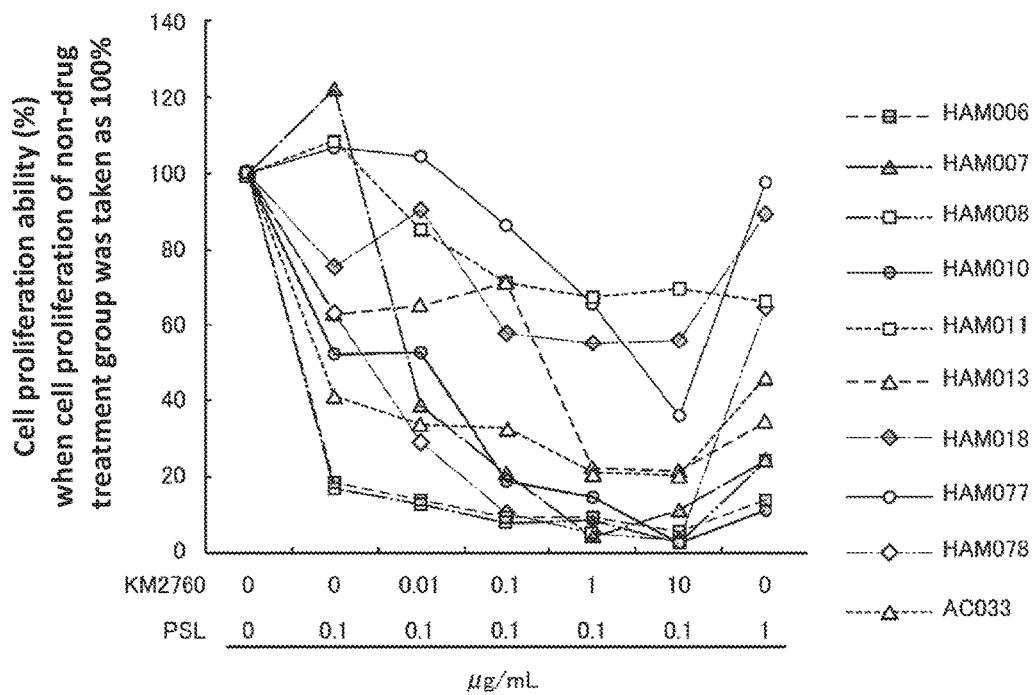
FIG. 3A represents inhibitory effects of combination treatment of anti-human CCR4 chimeric antibody KM2760 and prednisolone on spontaneous cell proliferation in PBMCs derived from HAM patients and asymptomatic HTLV-1 carriers (ACs). It represents spontaneous cell proliferation of each patient sample. The vertical axis represents cell proliferation ability (%) when cell proliferation of non-drug treatment group was taken as 100%, and the horizontal axis represents drugs added.
Figure 3B:
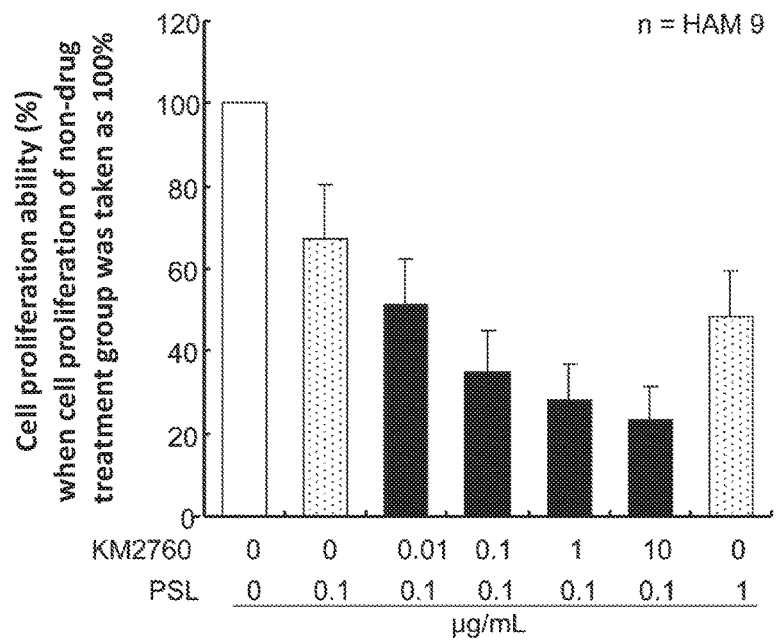
FIG. 3B represents the mean value of the samples of 9 HAM patients of FIG. 3A. It represents inhibitory effects of combination treatment of anti-human CCR4 chimeric antibody KM2760 and prednisolone on spontaneous cell proliferation in PBMCs derived from HAM patients and asymptomatic HTLV-1 carriers (ACs). The vertical axis represents cell proliferation ability (%) when cell proliferation of non-drug treatment group was taken as 100%, and the horizontal axis represents the concentrations of drugs added.

The combination effect of KM2760 with PSL was also confirmed in asymptomatic HTLV-1 carriers (FIG. 3A).

Meanwhile, with respect to the amount of HTLV-1 proviral DNA in PBMCs of HAM patients, 0.1 or 1 μg/mL of prednisolone almost didn't reduce the amount of HTLV-1 proviral DNA, compared to non-drug treatment.

Figure 3C:
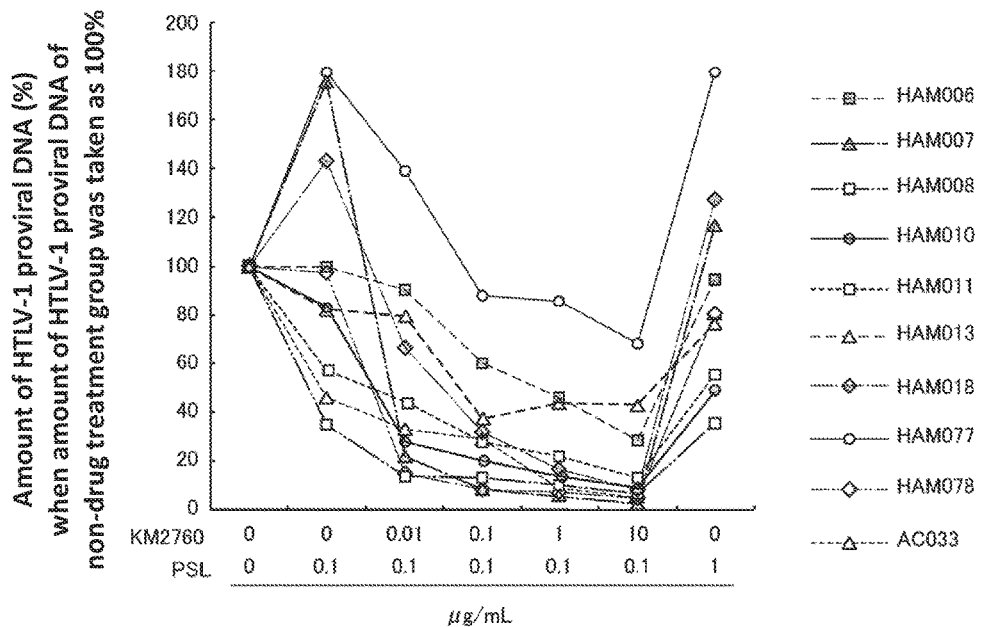
FIG. 3C represents inhibitory effects of combination treatment of anti-human CCR4 chimeric antibody KM2760 and prednisolone on the amount of HTLV-1 proviral DNA in PBMCs derived from HAM patients and asymptomatic HTLV-1 carriers (ACs). It represents the amount of HTLV-1 proviral DNA of each patient sample. The vertical axis represents the amount of HTLV-1 proviral DNA (%) when the amount of HTLV-1 proviral DNA of non-drug treatment group was taken as 100%, and the horizontal axis represents the concentrations of drugs added.
Figure 3D:
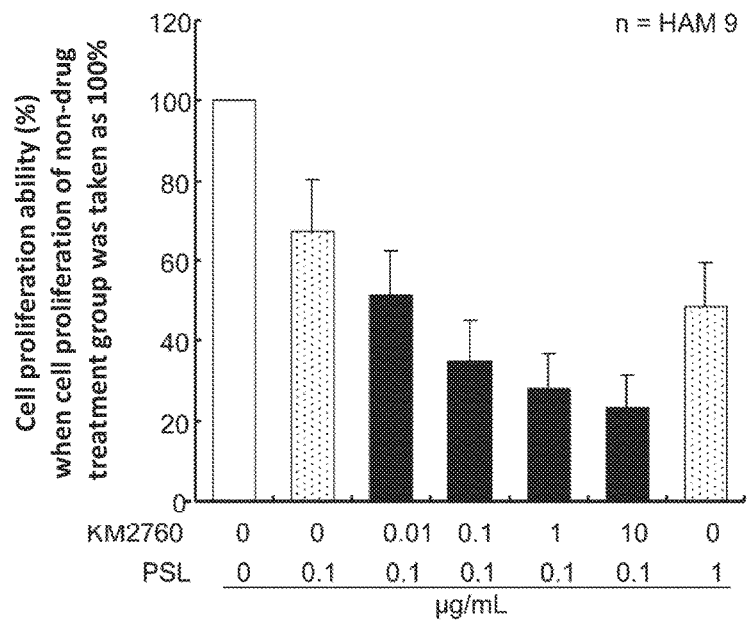
FIG. 3D represents the mean value of the samples of 9 HAM patients of FIG. 3C. The vertical axis represents the amount of HTLV-1 proviral DNA (%) when the amount of HTLV-1 proviral DNA of non-drug treatment group was taken as 100%, and the horizontal axis represents the concentrations of drugs added.

However, combination treatment of 0.1 μg/mL of PSL with KM2760 remarkably reduced the amount of HTLV-1 proviral DNA in an antibody concentration-dependent manner, compared to non-drug treatment, and 0.1 μg/mL PSL+ 10 μg/mL KM2760 reduced the amount of HTLV-1 proviral DNA to approximately 20%, compared to non-drug treatment (FIG. 3D).

The combination effect of KM2760 with PSL was also confirmed in asymptomatic HTLV-1 carriers (FIG. 3C).

Figure 3E:
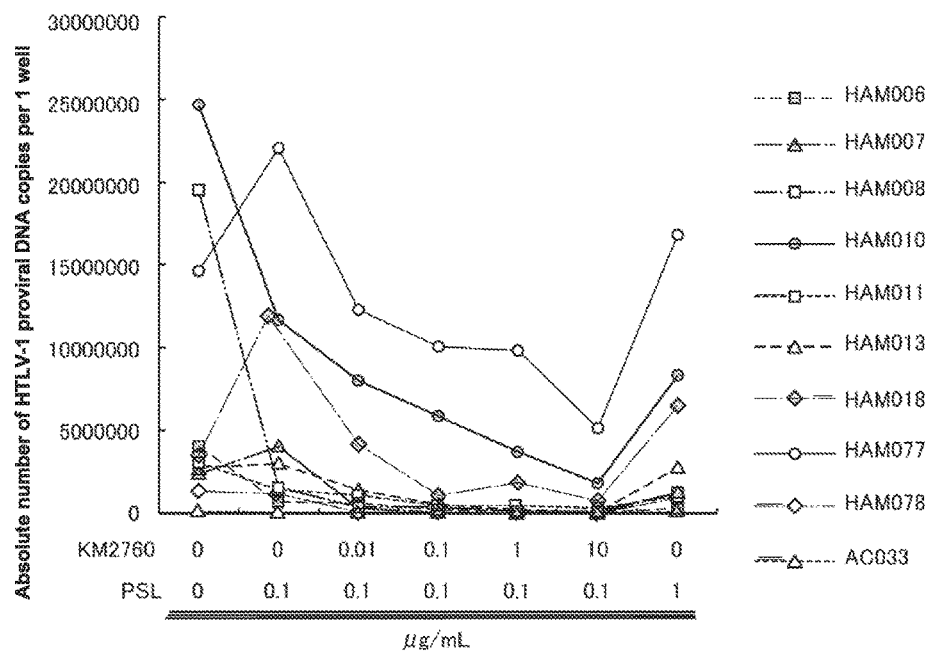
FIG. 3E represents inhibitory effects of combination treatment of anti-human CCR4 chimeric antibody KM2760 and prednisolone on the absolute amount of HTLV-1 proviral DNA in PBMCs derived from HAM patients and asymptomatic HTLV-1 carriers (ACs). It represents the absolute number of HTLV-1 proviral DNA copies per each well of each patient sample. The vertical axis represents the absolute number of HTLV-1 proviral DNA copies per 1 well, and the horizontal axis represents drugs added.
Figure 3F:
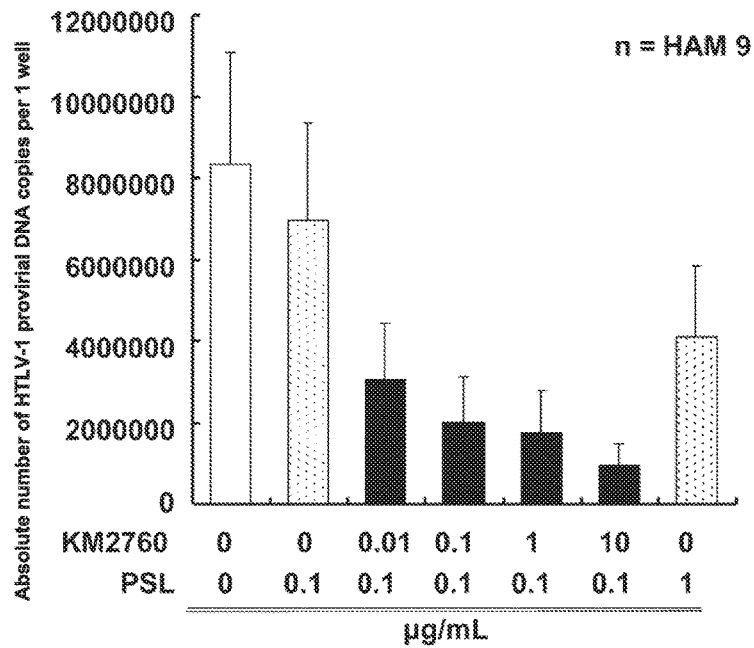
FIG. 3F represents the mean value of the samples of 9 HAM patients of FIG. 3E. The vertical axis represents the absolute number of HTLV-1 proviral DNA copies per 1 well, and the horizontal axis represents drugs added.

Further, the result of quantifying the absolute amount of HTLV-1 proviral DNA of each well (FIGS. 3E and 3F) showed that 1 μg/mL of PSL reduced the absolute amount of HTLV-1 proviral DNA to approximately 50%, compared to non-drug treatment, but PSL+KM2760 further reduced the absolute amount of HTLV-1 proviral DNA to a lower percentage in all wells of any concentration.

Therefore, it was revealed that the amount of HTLV-1 proviral DNA in PBMCs of HAM patients was more strongly reduced by combination treatment of the low dose of PSL with anti-human CCR4 antibody. Namely adrenocorticosteroid and anti-human CCR4 antibody synergistically effect on the amount of HTLV-1 proviral DNA in PBMCs of HAM patients.

These results suggest that high therapeutic effect can be obtained by combination of the low dose of adrenocorticosteroid drug with anti-human CCR4 antibody.

Further, the use of the low dose of adrenocorticosteroid drug makes it possible to apply the adrenocorticosteroid drug to the therapy for a longer period of time than before, and reduces frequency of adverse events accompanied by the use of adrenocorticosteroid drug.

[Example 4] Inhibitory Effect of Anti-Human CCR4 Antibody and Adrenocorticosteroid Drug on Cytokine Production In order to examine the inhibitory effect of anti-human CCR4 antibody and adrenocorticosteroid drug on inflammatory cytokine production in PBMCs of HAM patients, PBMCs of HAM patients were cultured, and the concentrations of IFN-γ, TNF-α, IL-2, IL-6 and IL-10 in the culture supernatants were measured.

PBMCs of HAM patients were cultured for 7 days in the same manner as in Example 2, and the culture supernatants were recovered after cultivation. The concentrations of the cytokines were measured using kits for measuring cytokine concentrations (all manufactured by BD Biosciences), Human IFNγ Flex kit (cat. 560111), Human TNFα Flex kit (cat. 560122), Human IL-6 Flex kit (cat. 558276), Human IL-2 Flex kit (cat. 558270) and Human IL-10 Flex kit (cat. 558274) by BD™ Cytometric Bead Array (CBA) (FIGS. 4A, 4B, 5A, 5B, 6A, 6B, 7A, 7B, 8A and 8B).

Figure 4A:
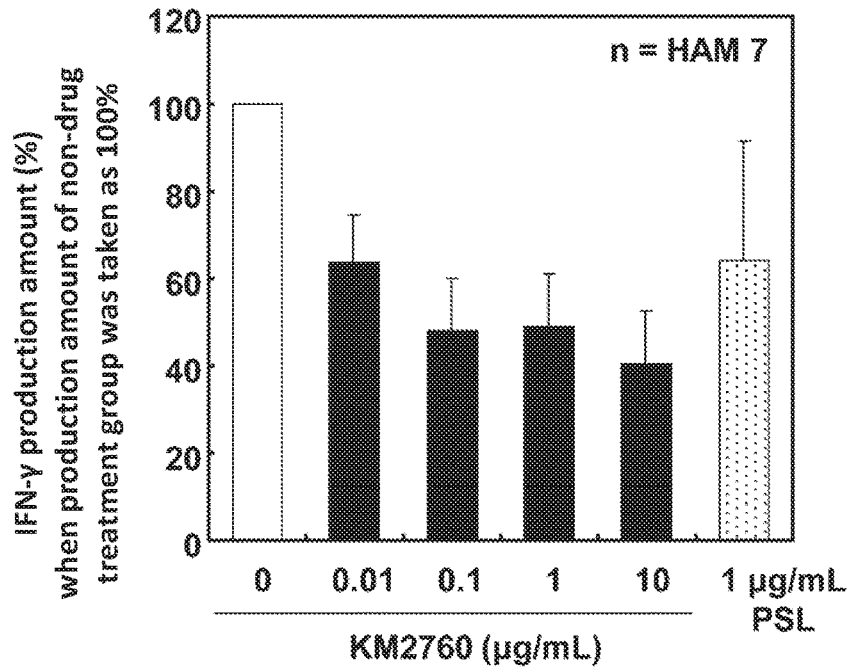
FIG. 4A represents inhibitory effects of anti-human CCR4 chimeric antibody KM2760 and prednisolone on IFN-γ production in PBMCs of 7 HAM patients. It represents the effect of KM2760 alone. The vertical axis represents the amount of IFN-γ production (%) when the production amount of non-drug treatment group was taken as 100%, and the horizontal axis represents drugs added and concentrations thereof.
Figure 4B:
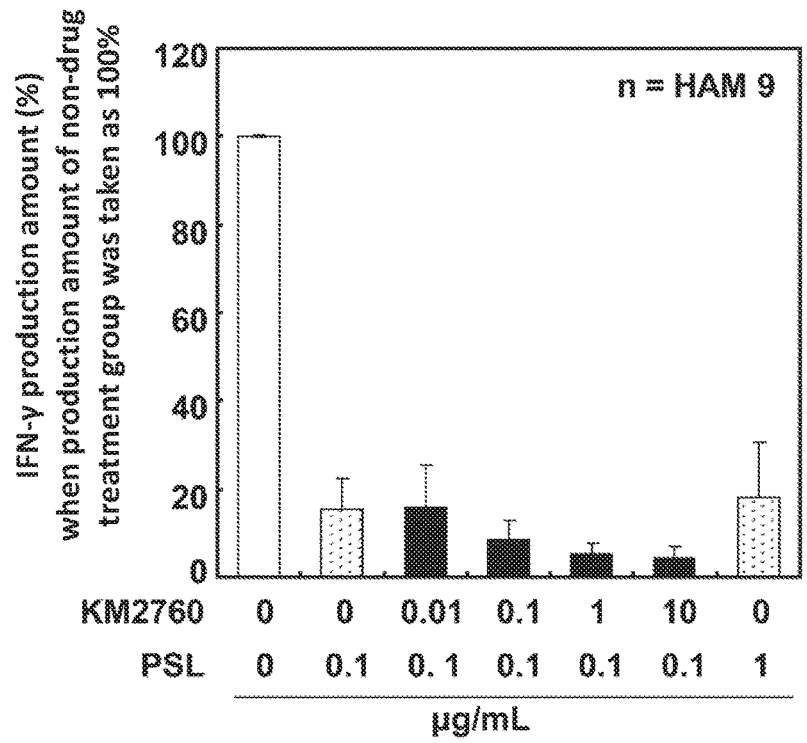
FIG. 4B represents inhibitory effects of anti-human CCR4 chimeric antibody KM2760, prednisolone, and combination treatment thereof on IFN-γ production in PBMCs of HAM patients. It represents the effect of combination treatment of KM2760 and prednisolone. The vertical axis represents the amount of IFN-γ production (%) when the production amount of non-drug treatment group was taken as 100%, and the horizontal axis represents drugs added and concentrations thereof.

As a result, compared to non-drug treatment, KM2760 inhibited IFN-γ production to approximately 50% (FIG. 4A), whereas combination treatment of KM2760+PSL inhibited IFN-γ production to approximately 10-20% (FIG. 4B).

Figure 5A:
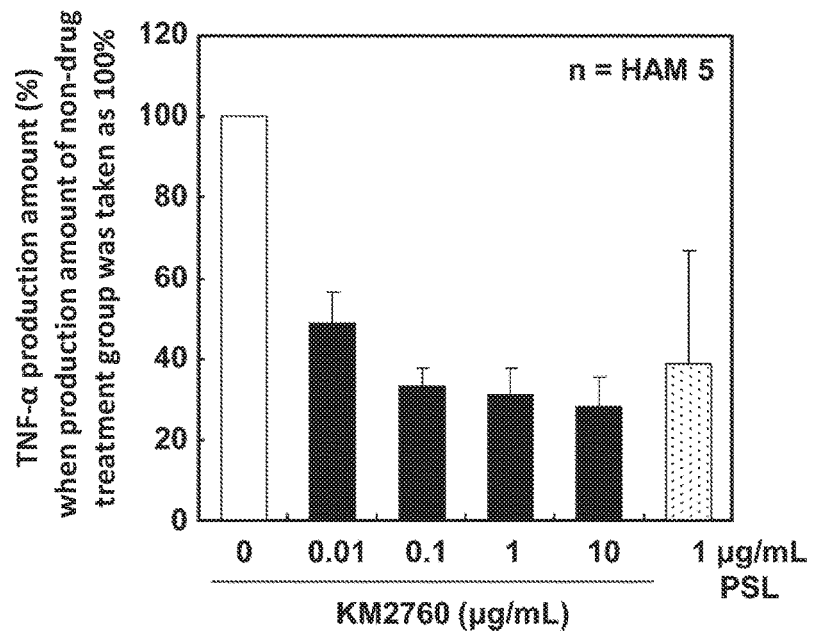
FIG. 5A represents inhibitory effects of anti-human CCR4 chimeric antibody and prednisolone on TNF-α production in PBMCs of 5 HAM patients. It represents the effect of KM2760 alone. The vertical axis represents the amount of TNF-α production (%) when the production amount of non-drug treatment group was taken as 100%, and the horizontal axis represents drugs added and concentrations thereof.
Figure 5B:
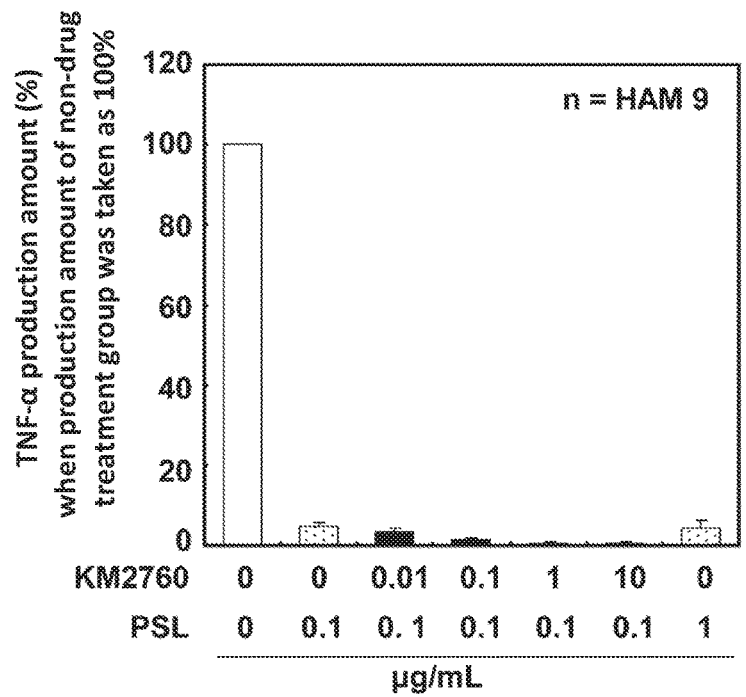
FIG. 5B represents inhibitory effects of anti-human CCR4 chimeric antibody KM2760, prednisolone, and combination treatment thereof on TNF-α production in PBMCs of 9 HAM patients. It represents the effect of combination treatment of KM2760 and prednisolone. The vertical axis represents the amount of TNF-α production (%) when the production amount of non-drug treatment group was taken as 100%, and the horizontal axis represents drugs added and concentrations thereof.

Compared to non-drug treatment, KM2760 inhibited TNF-α production to approximately 30% (FIG. 5A), whereas combination treatment of KM2760+PSL inhibited TNF-α production to approximately 10% or less (FIG. 5B).

Figure 6A:
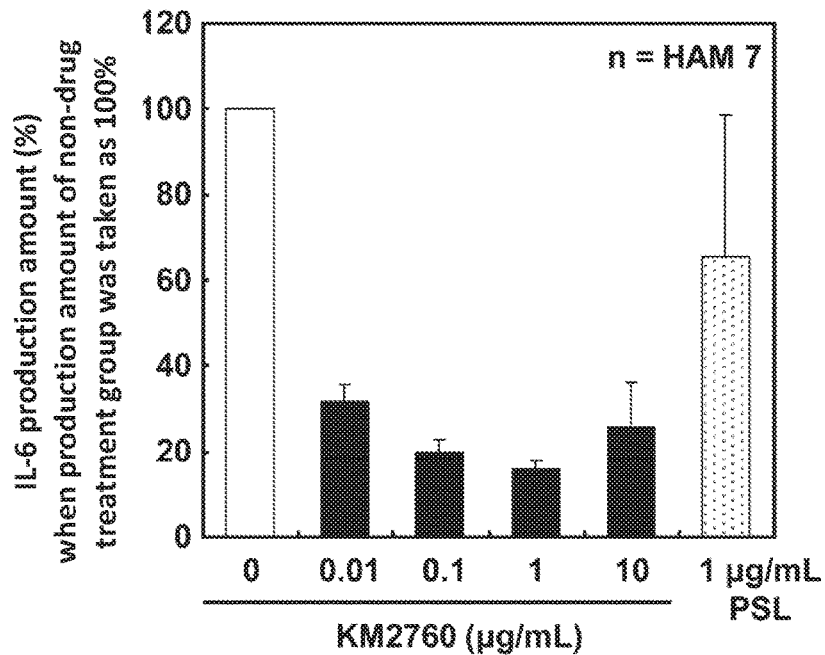
FIG. 6A represents inhibitory effects of anti-human CCR4 chimeric antibody KM2760 and prednisolone on IL-6 production in PBMCs of 7 HAM patients. It represents the effect of KM2760 alone. The vertical axis represents the amount of IL-6 production (%) when the production amount of non-drug treatment group was taken as 100%, and the horizontal axis represents drugs added and concentrations thereof.
Figure 6B:
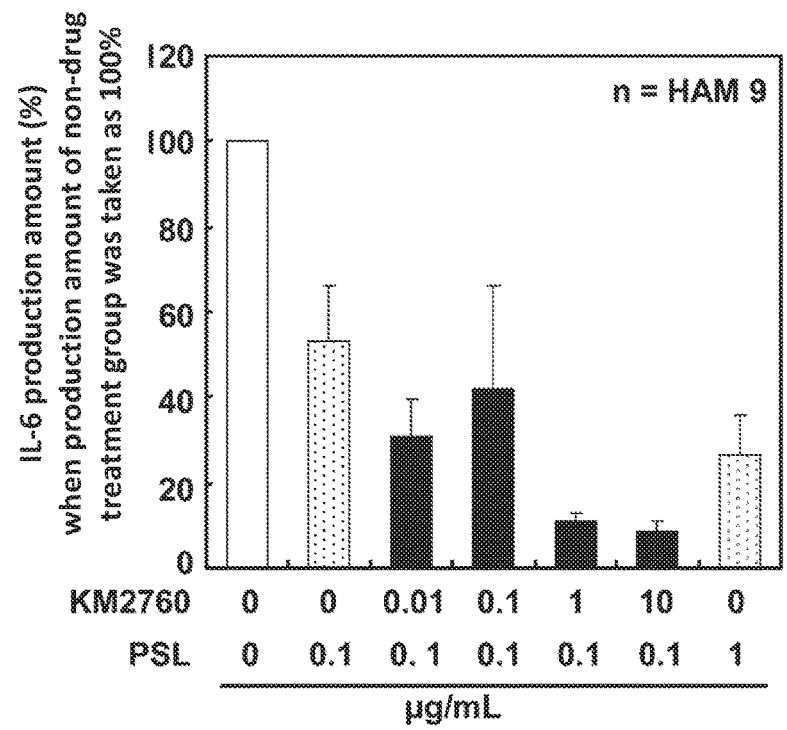
FIG. 6B represents inhibitory effects of anti-human CCR4 chimeric antibody KM2760, prednisolone, and combination treatment thereof on IL-6 production in PBMCs of 9 HAM patients. It represents the effect of combination treatment of KM2760 and prednisolone. The vertical axis represents the amount of IL-6 production (%) when the production amount of non-drug treatment group was taken as 100%, and the horizontal axis represents drugs added and concentrations thereof.

Compared to non-drug treatment, KM2760 inhibited IL-6 production to approximately 20% (FIG. 6A), whereas combination treatment of KM2760+PSL inhibited IL-6 production to approximately 10-20% (FIG. 6B).

Figure 7A:
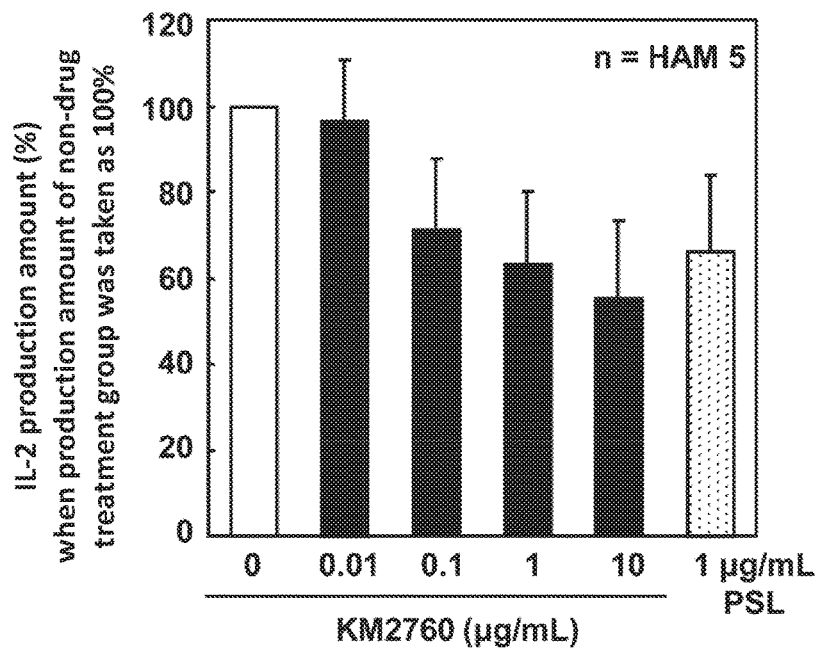
FIG. 7A represents inhibitory effects of anti-human CCR4 chimeric antibody KM2760 and prednisolone on IL-2 production in PBMCs of 5 HAM patients. It represents the effect of KM2760 alone. The vertical axis represents the amount of IL-2 production (%) when the production amount of non-drug treatment group was taken as 100%, and the horizontal axis represents drugs added and concentrations thereof.
Figure 7B:
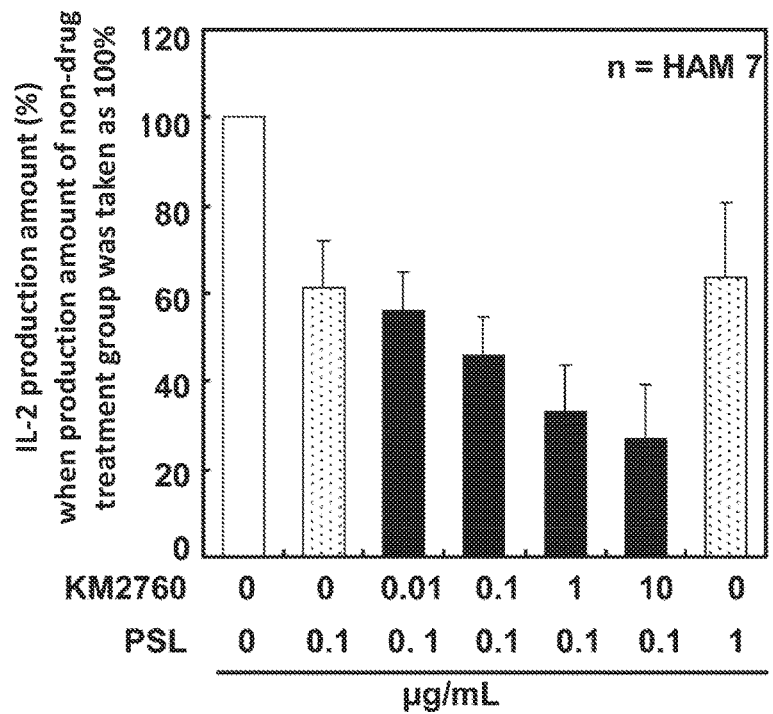
FIG. 7B represents inhibitory effects of anti-human CCR4 chimeric antibody KM2760, prednisolone, and combination treatment thereof on IL-2 production in PBMCs of 7 HAM patients. It represents the effect of combination treatment of KM2760 and prednisolone. The vertical axis represents the amount of IL-2 production (%) when the production amount of non-drug treatment group was taken as 100%, and the horizontal axis represents drugs added and concentrations thereof.

Compared to non-drug treatment, KM2760 inhibited IL-2 production to approximately 60-70% (FIG. 7A), whereas combination treatment of KM2760+PSL inhibited IL-2 production to approximately 30-60% (FIG. 7B).

Figure 8A:
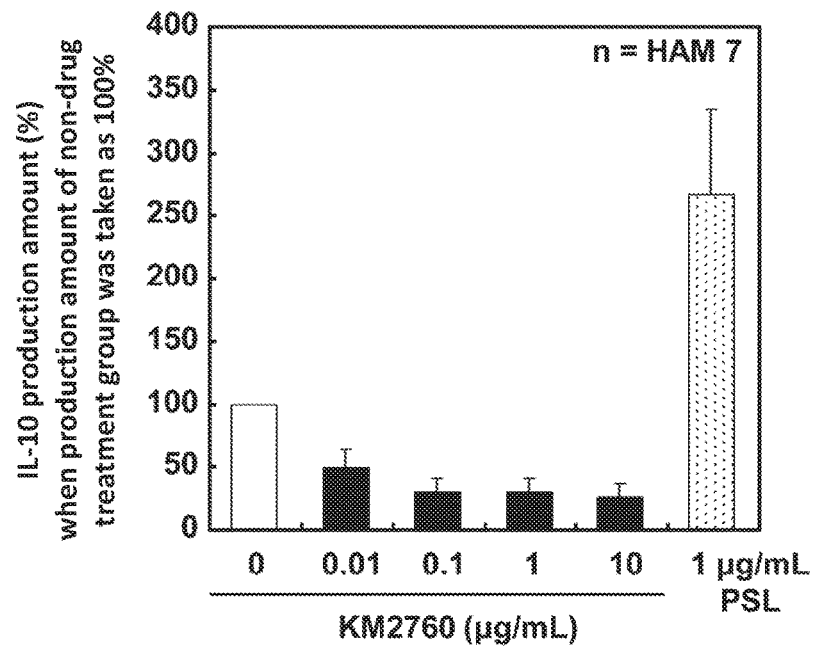
FIG. 8A represents inhibitory effects of anti-human CCR4 chimeric antibody KM2760 and predonisolone on IL-10 production in PBMCs of 7 HAM patients. It represents the effect of KM2760 alone. The vertical axis represents the amount of IL-10 production (%) when the production amount of non-drug treatment group was taken as 100%, and the horizontal axis represents drugs added and concentrations thereof.
Figure 8B:
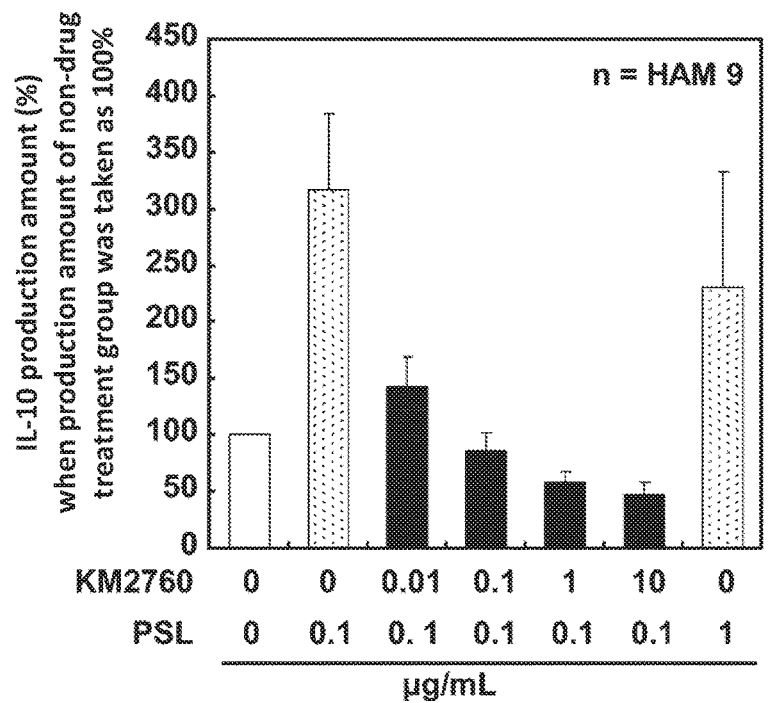
FIG. 8B represents inhibitory effects of anti-human CCR4 chimeric antibody KM2760, prednisolone, and combination treatment thereof on IL-10 production in PBMCs of 9 HAM patients. It represents the effect of combination treatment of KM2760 and prednisolone. The vertical axis represents the amount of IL-10 production (%) when the production amount of non-drug treatment group was taken as 100%, and the horizontal axis represents drugs added and concentrations thereof.

Compared to non-drug treatment, KM2760 inhibited IL-10 production to approximately 50% (FIG. 8A), and combination treatment of KM2760+PSL inhibited IL-10 production to a similar degree (FIG. 8B).

Taken together, anti-human CCR4 chimeric antibody KM2760 inhibited the production of all cytokines, IFN-γ, TNF-α, IL-2, IL-6 and IL-10 produced in PBMCs derived from HAM patients in an antibody concentration-dependent manner, whereas prednisolone inhibited the production of all cytokines, IFN-γ, TNF-α, IL-2 and IL-6, except IL-10.

Further, combination treatment of 0.1 μg/mL PSL+0.01 μg/mL-10 μg/mL KM2760 more strongly inhibited IFN-γ, TNF-α, and IL-2 productions than KM2760 alone, and slightly more strongly inhibited IL-6 production, compared to KM2760 alone. Combination treatment of PSL+KM2760 did not affect IL-10 production.

Therefore, it is suggested that because the anti-human CCR4 antibody inhibits production of inflammatory cytokines in PBMCs of HAM patients, the anti-human CCR4 antibody is able to inhibit chronic inflammation by inhibiting CD4$^+$ CD25$^+$ CCR4$^+$ Foxp3lowIFN-$\gamma^+$ T cells (T$_{HAM}$) and by suppressing proliferation of Tax-specific CD8$^+$ T cells.

It is also suggested that because productions of Th1 cytokines, IFN-$\gamma$, TNF-$\alpha$ and IL-2 can be more effectively inhibited by combination treatment with the low dose of adrenocorticosteroid drug, T$_{HAM}$, a pathogenic cell of HAM, can be inhibited and proliferation of Tax-specific CD8$^+$ T cells can be also inhibited.

[Example 5] Inhibitory Effect of Anti-Human CCR4 Antibody on Spinal Fluid Cells of HAM Patients Referring to that the anti-human CCR4 antibody has the inhibitory effects on the PBMC cell proliferation of HAM patients, the amount of HTLV-1 proviral DNA, and the cytokine production, the effect of anti-human CCR4 antibody on spinal fluid-derived cells of HAM patients was examined.

Figure 9A:
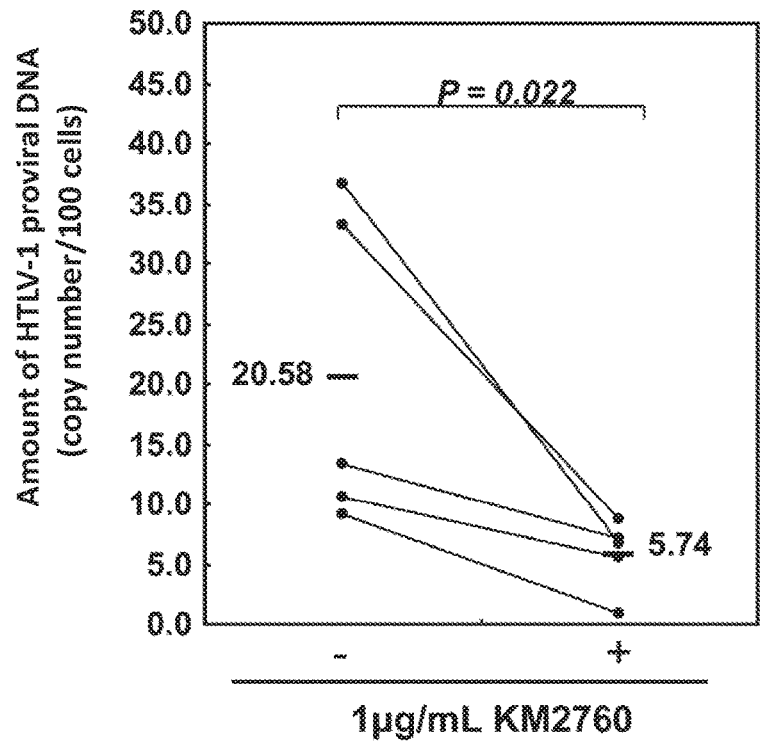
FIG. 9A represents inhibitory effects of anti-human CCR4 chimeric antibody KM2760 on HTLV-1 proviral DNA amount in the spinal fluid cells of HAM patients. The vertical axis represents the amount of HTLV-1 proviral DNA (copy number/100 cells), and the horizontal axis represents the presence and absence of KM2760 (antibody concentration is 1 mg/ml).
Figure 9B:
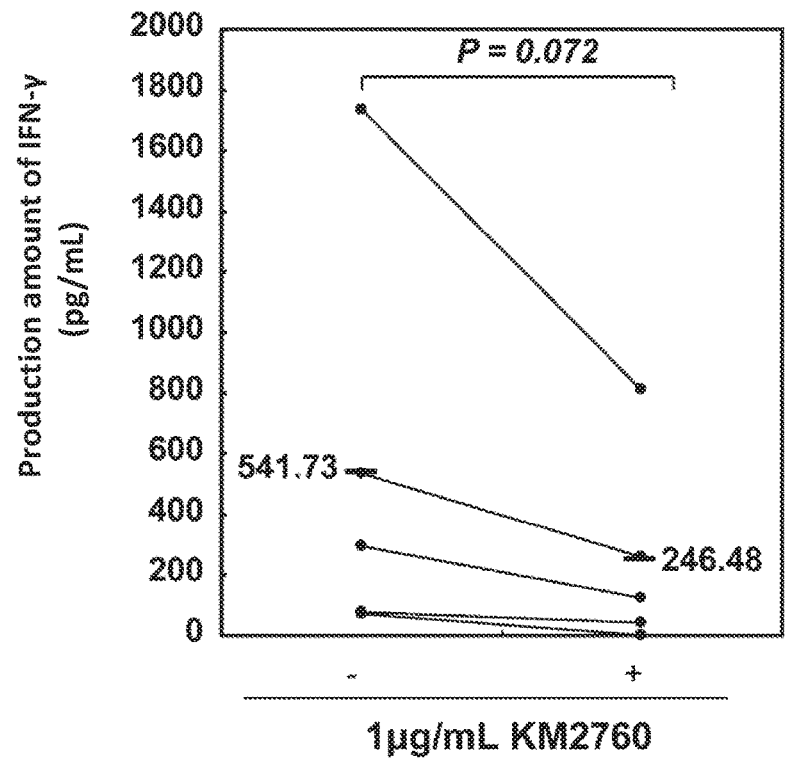
FIG. 9B represents inhibitory effects of anti-human CCR4 chimeric antibody KM2760 on IFN-γ production in the spinal fluid cells of HAM patients. The vertical axis represents the production amount of IFN-γ (pg/mL), and the horizontal axis represents antibody concentration. The solid line represents the mean value of each group.

Spinal fluid cells were isolated from cerebrospinal fluids (hereinafter, abbreviated to CSF) collected from 5 HAM patients, and cultured in the same manner as in Examples 1-3 in the presence or absence of 1 µg/mL of anti-human CCR4 chimeric antibody KM2760 for 7 days. After cultivation, the amount of HTLV-1 proviral DNA (FIG. 9A) and the IFN-$\gamma$ production amount in the culture supernatant (FIG. 9B) were measured.

As a result, when the spinal fluid cells derived from HAM patients were treated with KM2760, the amounts of HTLV-1 proviral DNA were reduced to ¼ and the amounts of IFN-$\gamma$ produced were reduced to ½, compared to those treated with no drug. Therefore, it was revealed that the anti-human CCR4 antibody reduces the amount of HTLV-1 proviral DNA in spinal fluid cells of HAM patients and also inhibits IFN-$\gamma$ production.

These results suggest that in the spinal cord region observed as chronic inflammation findings, the infection rate of spinal fluid cells can be reduced by reducing the HTLV-1 proviral DNA amount, and cytotoxic immune reactions can be inhibited by suppressing production of the Th1 cytokine, IFN-$\gamma$.

[Example 6] Therapeutic Effect of Anti-Human CCR4 Antibody on PBMCs of HAM Patients Inhibitory effects of anti-human CCR4 chimeric antibody KM2760 and anti-human CCR4 humanized antibody Poteligeo® (manufactured by Kyowa Hakko Kirin co., Ltd.) on spontaneous cell proliferation, the amount of HTLV-1 provirus DNA, and the cytokine production in PBMCs of HAM patients (N=11) were examined in the same manner as in Examples 1, 2, and 4.

Figure 10A:
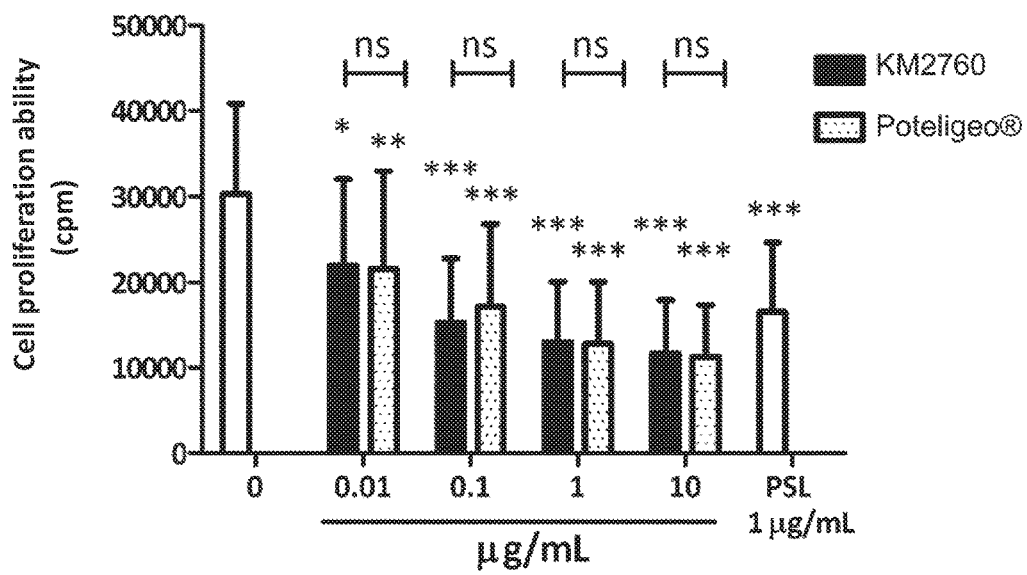
FIG. 10A represents inhibitory effects of anti-human CCR4 chimeric antibody KM2760 and anti-human CCR4 humanized antibody Poteligeo® on spontaneous cell proliferation (N=12) of PBMCs derived from HAM patients. The vertical axis represents cell proliferation ability (cpm) by i $^3$H-thymidine up-take in PBMCs derived from each patient and the horizontal axis represents antibody concentration (m/mL). Comparison with non-antibody treatment: Repeated measures ANOVA with Dunnett's post-test, Comparison between antibodies of the same concentrations: paired t-test was performed to test a significant difference. 1 μg/mL of prednisolone (PSL) was used as a positive control.
Figure 10B:
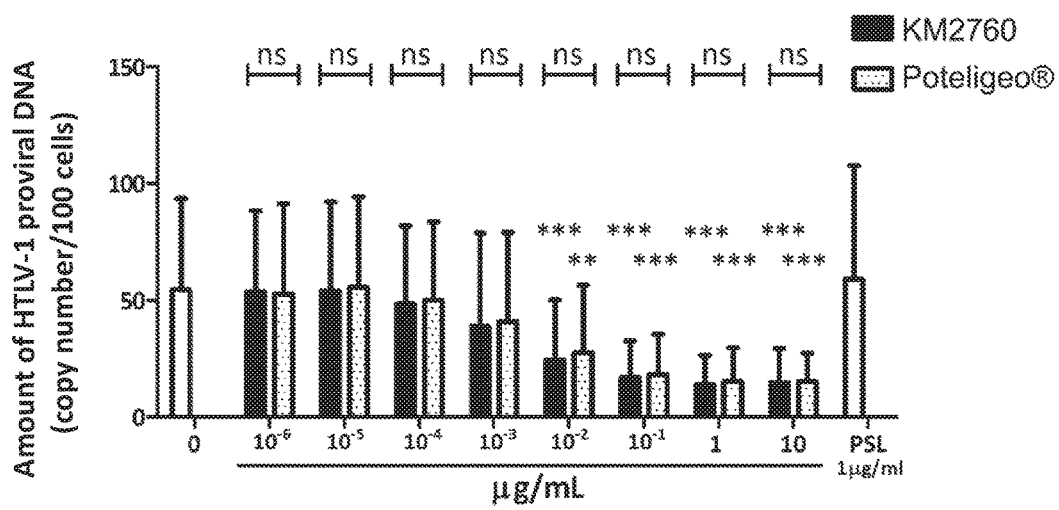
FIG. 10B represents inhibitory effects of anti-human CCR4 chimeric antibody KM2760 and anti-human CCR4 humanized antibody Poteligeo® on HTLV-1 proviral DNA amount (N=5) in PBMCs of HAM patients. The vertical axis represents the amount of HTLV-1 proviral DNA (copy number/100 cells), and the horizontal axis represents antibody concentration. Comparison with non-antibody treatment: Repeated measures ANOVA with Dunnett's post-test, Comparison between antibodies of the same concentrations: paired t-test was performed to test a significant difference. 1 μg/mL of prednisolone (PSL) was used as a positive control.
Figure 11A:
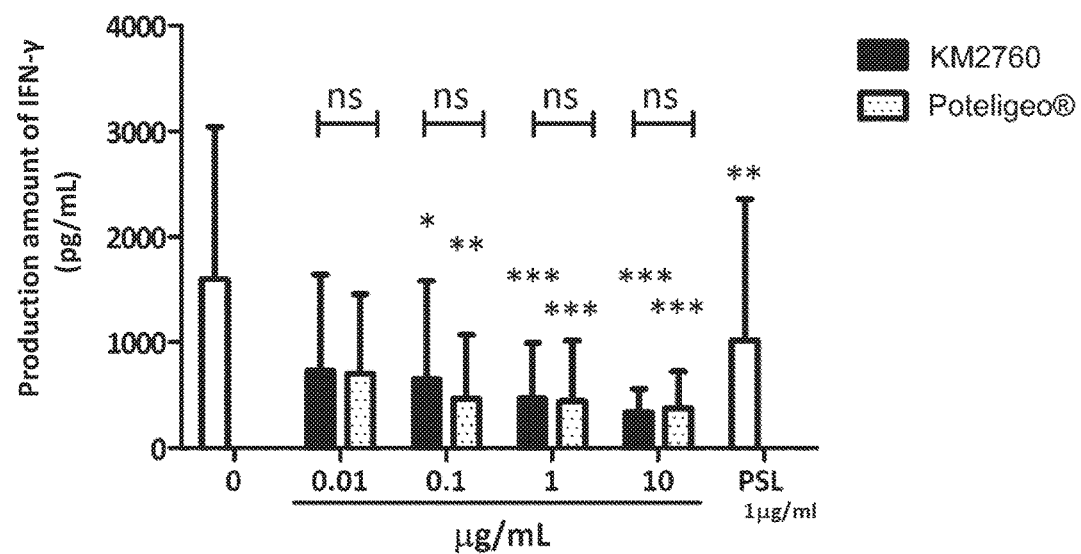
FIG. 11A represents inhibitory effects of anti-human CCR4 chimeric antibody KM2760 and anti-human CCR4 humanized antibody Poteligeo® on IFN-γ production in PBMCs of HAM patients. The vertical axis represents the production amount of IFN-γ (pg/mL), and the horizontal axis represents antibody concentration (m/mL). 1 μg/mL of prednisolone (PSL) was used as a positive control. Comparison with non-antibody treatment: Friedman's test with Dunn's post test, Comparison between antibodies of the same concentrations: Wilcoxon matched pairs test was performed to test a significant difference.
Figure 11B:
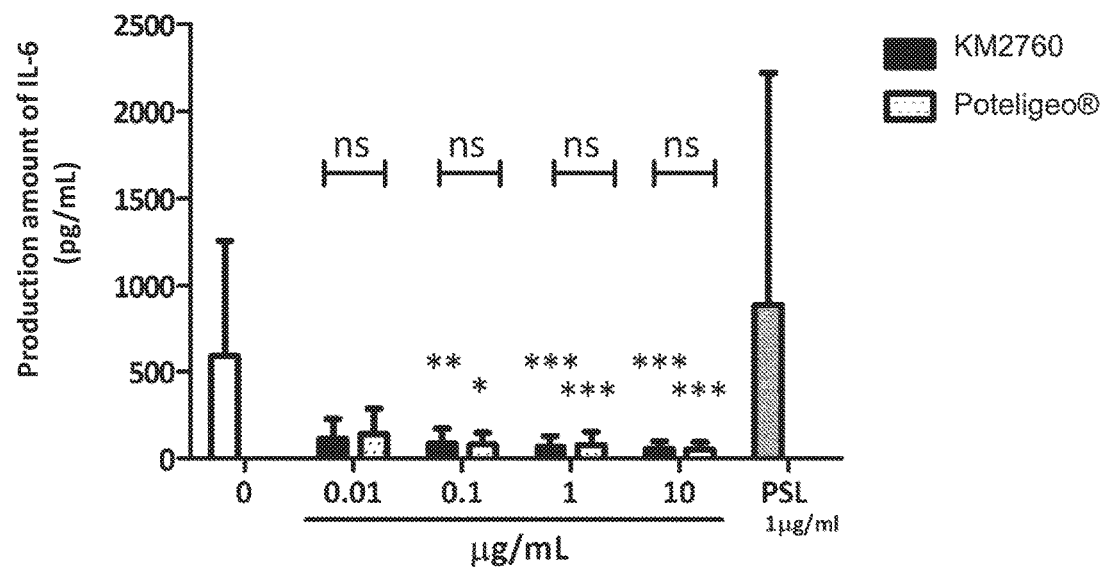
FIG. 11B represents inhibitory effects of anti-human CCR4 chimeric antibody KM2760 and anti-human CCR4 humanized antibody Poteligeo® on IL-6 production in PBMCs of HAM patients. The vertical axis represents the production amount of IL-6 (pg/mL), and the horizontal axis represents antibody concentration (m/mL). 1 μg/mL of prednisolone (PSL) was used as a positive control. Comparison with non-antibody treatment: Friedman's test with Dunn's post test, Comparison between antibodies of the same concentrations: Wilcoxon matched pairs test was performed to test a significant difference.
Figure 11C:
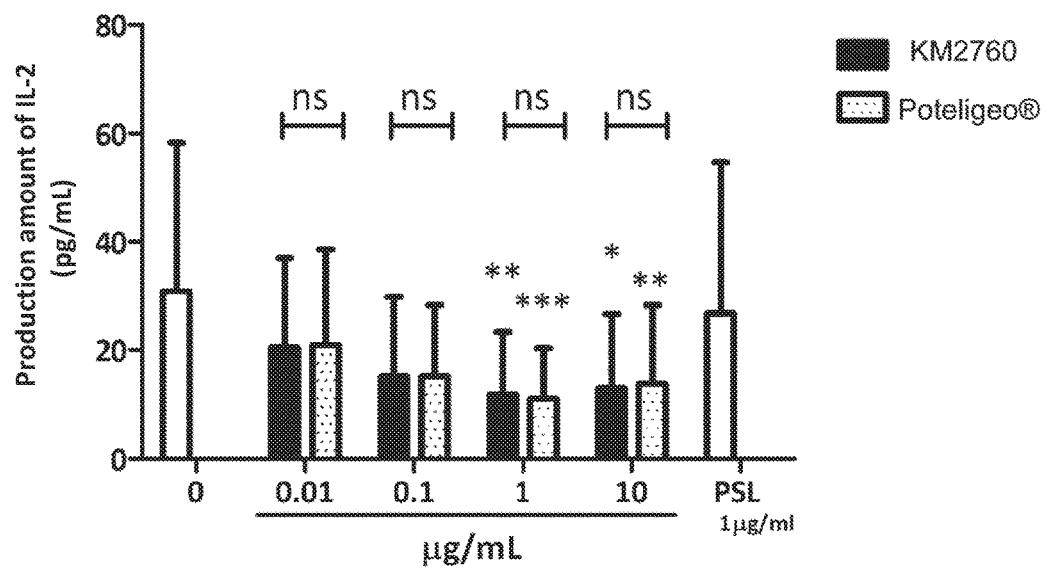
FIG. 11C represents inhibitory effects of anti-human CCR4 chimeric antibody KM2760 and anti-human CCR4 humanized antibody Poteligeo® on IL-2 production in PBMCs of HAM patients. The vertical axis represents the production amount of IL-2 (pg/mL), and the horizontal axis represents antibody concentration (m/mL). 1 µg/mL of prednisolone (PSL) was used as a positive control. Comparison with non-antibody treatment: Friedman's test with Dunn's post test, Comparison between antibodies of the same concentrations: Wilcoxon matched pairs test was performed to test a significant difference.
Figure 11D:
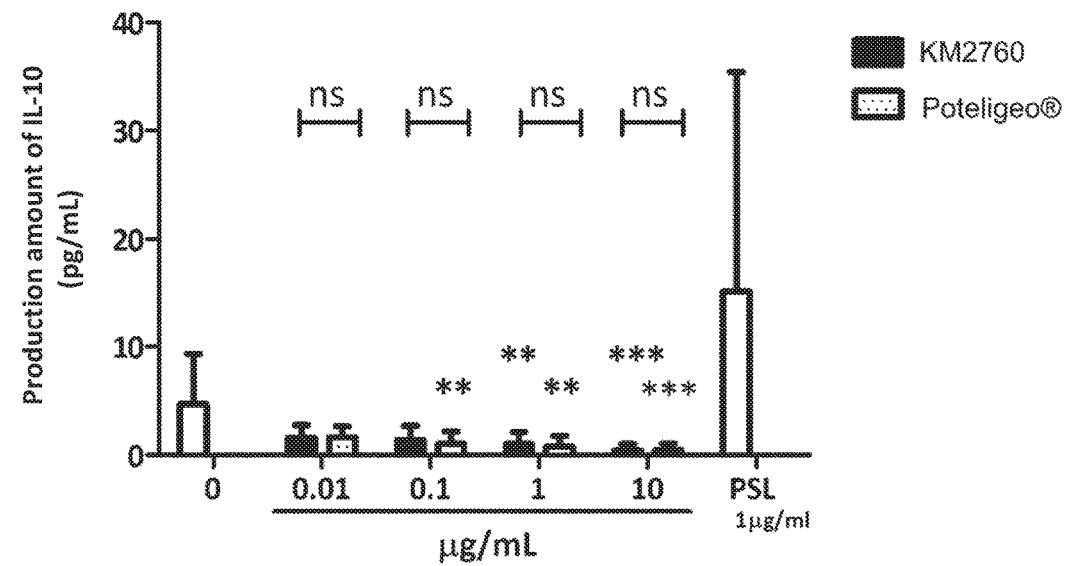
FIG. 11D represents inhibitory effects of anti-human CCR4 chimeric antibody KM2760 and anti-human CCR4 humanized antibody Poteligeo® on IL-10 production in PBMCs of HAM patients. The vertical axis represents the production amount of IL-10 (pg/mL), and the horizontal axis represents antibody concentration (m/mL). 1 µg/mL of prednisolone (PSL) was used as a positive control. Comparison with non-antibody treatment: Friedman's test with Dunn's post test, Comparison between antibodies of the same concentrations: Wilcoxon matched pairs test was performed to test a significant difference.
Figure 11E:
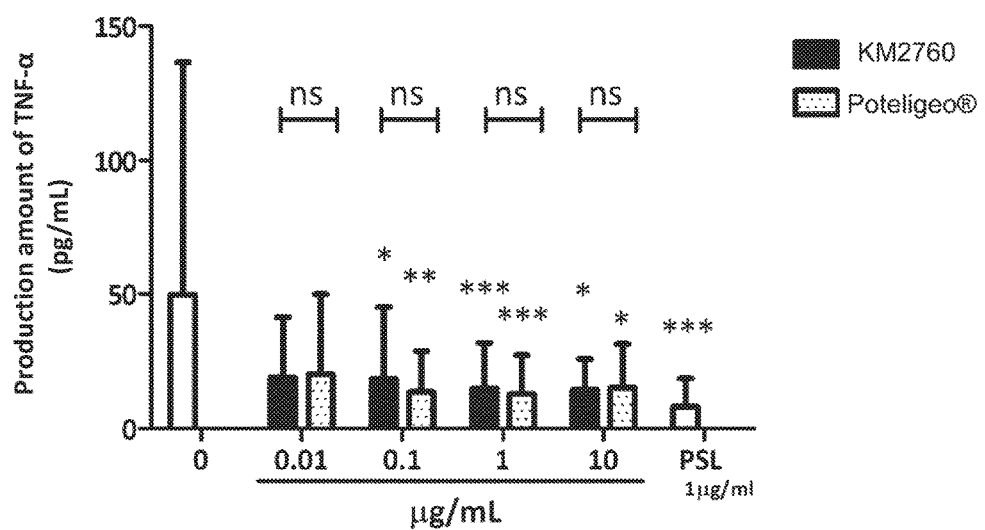
FIG. 11E represents inhibitory effects of anti-human CCR4 chimeric antibody KM2760 and anti-human CCR4 humanized antibody Poteligeo® on TNF-α production in PBMCs of HAM patients. The vertical axis represents the production amount of TNF-α (pg/mL), and the horizontal axis represents antibody concentration (m/mL). 1 µg/mL of prednisolone (PSL) was used as a positive control. Comparison with non-antibody treatment: Friedman's test with Dunn's post test, Comparison between antibodies of the same concentrations: Wilcoxon matched pairs test was performed to test a significant difference.

As a result, the anti-human CCR4 chimeric antibody KM2760 and anti-human CCR4 humanized antibody Poteligeo® inhibited spontaneous cell proliferation (FIG. 10A), the amount of HTLV-1 provirus DNA (FIG. 10B), and the cytokine production (FIG. 11A-11E) in PBMCs of HAM patients in an almost similar way.

Therefore, it was suggested that the anti-human CCR4 humanized antibody Poteligeo® already launched can be a therapeutic agent for HAM patients and ACs.

SEQ ID NO. 7: Description of Artificial Sequence; variable region of humanized antibody H chain SEQ ID NO. 8: Description of Artificial Sequence; variable region of humanized antibody L chain Although the present invention has been described in detail and with reference to specific embodiments, it is apparent to those skilled in the art that various changes and modifications can be made without departing from the spirit and scope of the present invention. Incidentally, the present application is based on a US provisional patent application filed on Jul. 6, 2012 (U.S. Patent Application No. 61/668,686), the entire content of which is incorporated herein by reference.

The invention claimed is:

1. A therapeutic method, comprising reducing expression level of a cytokine produced by a human T cell leukemia virus type-1 (HTLV-1)-infected cell in a HTLV-1 associated myelopathy (HAM) patient or an asymptomatic HTLV-1 carrier (AC), by administering an anti-human CC-chemokine receptor 4 (CCR4) antibody to the HAM patient or the AC.

2. The therapeutic method according to claim 1, comprising reducing HTLV-1 virus-infected cells.

3. The therapeutic method according to claim 1, comprising reducing the amount of HTLV-1 proviral DNA in the HAM patients.

4. The therapeutic method according to claim 1, comprising reducing cell proliferation of the HTLV-1 virus-infected cell.

5. The therapeutic method according to claim 1, wherein the HTLV-1 virus-infected cell is CCR4$^+$T cell.

6. The therapeutic method according to claim 1, wherein the cytokine is any one selected from the group consisting of interferon $\gamma$ (IFN-$\gamma$), tumor necrosis factor $\alpha$ (TNF-$\alpha$), interleukin (IL)-2 (IL-2), IL-6, IL-10 and IL-17.

7. The therapeutic method according to claim 1, further comprising administering one or more of an immunosuppressant and an anti-viral agent.

8. The therapeutic method according to claim 7, wherein the immunosuppressant is selected from the group consisting of prednisolone, methylprednisolone, dexamethasone, betamethasone, azathioprine, cyclosporine, tacrolimus, JAK inhibitor, NF$\kappa$B inhibitor, and a combination thereof.

9. The therapeutic method according to claim 1, further comprising administering a low dose of an immunosuppressant.

10. A method for reducing an expression level of a cytokine produced by a human T cell leukemia virus type-1 (HTLV-1)-infected cell in a HTLV-1 associated myelopathy (HAM) patient or an asymptomatic HTLV-1 carrier (AC), by administering an anti-human CC-chemokine receptor 4 (CCR4) antibody to the HAM patient or the AC.

11. The method according to claim 10, comprising reducing HTLV-1 virus-infected cells.

12. The method according to claim 10, comprising reducing an amount of HTLV-1 proviral DNA in the HAM patient.

13. The method according to claim 10, comprising reducing cell proliferation of the HTLV-1 virus-infected cell.

14. The method according to claim 10, wherein the HTLV-1 virus-infected cell is CCR4$^+$T cell.

15. The method according to claim 10, wherein the cytokine is any one selected from the group consisting of IFN-$\gamma$, TNF-$\alpha$, IL-2, IL-6, IL-10 and IL-17.

16. The method according to claim 10, further comprising administering one or more of an immunosuppressant and an anti-viral agent.

17. The method according to claim 16, wherein the immunosuppressant is any one selected from the group consisting of prednisolone, methylprednisolone, dexamethasone, betamethasone, azathioprine, cyclosporine, tacrolimus, JAK inhibitor, NFκB inhibitor, and a combination thereof.

18. The method according to claim 10, further comprising administering a low dose of an immunosuppressant.

* * * * *